US010568825B2

(12) United States Patent
Cetti et al.

(10) Patent No.: US 10,568,825 B2
(45) Date of Patent: *Feb. 25, 2020

(54) ANTIPERSPIRANT AND DEODORANT COMPOSITIONS

(71) Applicant: The Procter & Gamble Company, Cincinnati, OH (US)

(72) Inventors: Jonathan Robert Cetti, Mason, OH (US); Zerlina Guzdar Dubois, Mason, OH (US); Virginia Tzung-Hwei Hutchins, Cincinnati, OH (US); Michael Wayne Kinsey, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 351 days.

This patent is subject to a terminal disclaimer.

(21) Appl. No.: 14/105,549

(22) Filed: Dec. 13, 2013

(65) Prior Publication Data
US 2014/0170102 A1 Jun. 19, 2014

Related U.S. Application Data

(60) Provisional application No. 61/737,257, filed on Dec. 14, 2012, provisional application No. 61/869,241, filed on Aug. 23, 2013, provisional application No. 61/879,217, filed on Sep. 18, 2013.

(51) Int. Cl.
| A61K 8/49 | (2006.01) |
| A61K 8/40 | (2006.01) |
| A61Q 15/00 | (2006.01) |
| A61K 8/46 | (2006.01) |
| A61K 8/11 | (2006.01) |
| A61L 9/01 | (2006.01) |
| A61Q 5/02 | (2006.01) |
| A61Q 13/00 | (2006.01) |
| A61Q 19/00 | (2006.01) |
| A61Q 19/10 | (2006.01) |
| C11B 9/00 | (2006.01) |
| C11D 3/50 | (2006.01) |
| A61K 8/44 | (2006.01) |
| A61K 8/28 | (2006.01) |
| A61K 8/41 | (2006.01) |
| A61K 8/60 | (2006.01) |
| A61K 8/73 | (2006.01) |
| C11D 3/00 | (2006.01) |
| C11D 11/00 | (2006.01) |

(52) U.S. Cl.
CPC .............. A61K 8/496 (2013.01); A61K 8/11 (2013.01); A61K 8/28 (2013.01); A61K 8/40 (2013.01); A61K 8/41 (2013.01); A61K 8/445 (2013.01); A61K 8/46 (2013.01); A61K 8/49 (2013.01); A61K 8/494 (2013.01); A61K 8/4926 (2013.01); A61K 8/4986 (2013.01); A61K 8/602 (2013.01); A61K 8/738 (2013.01); A61L 9/01 (2013.01); A61Q 5/02 (2013.01); A61Q 13/00 (2013.01); A61Q 15/00 (2013.01); A61Q 19/00 (2013.01); A61Q 19/10 (2013.01); C11B 9/0011 (2013.01); C11B 9/0023 (2013.01); C11B 9/0084 (2013.01); C11B 9/0092 (2013.01); C11B 9/0096 (2013.01); C11D 3/001 (2013.01); C11D 3/502 (2013.01); C11D 11/0017 (2013.01); A61K 2800/56 (2013.01); A61K 2800/77 (2013.01)

(58) Field of Classification Search
None
See application file for complete search history.

(56) References Cited

U.S. PATENT DOCUMENTS

| 3,928,248 | A | * | 12/1975 | Mookherjee et al. ........ 512/22 |
| 4,262,030 | A | | 4/1981 | Winter et al. |
| 4,478,865 | A | | 10/1984 | Demole et al. |
| 5,538,719 | A | | 7/1996 | Preti et al. |
| 6,150,409 | A | | 11/2000 | Restrepo et al. |
| 6,306,818 | B1 | | 10/2001 | Anderson et al. |
| 7,585,833 | B2 | | 9/2009 | Fadel et al. |
| 7,722,807 | B2 | | 5/2010 | Keller, Jr. et al. |
| 7,763,238 | B2 | | 7/2010 | Preti et al. |
| 8,426,354 | B2 | | 4/2013 | Joichi et al. |
| 8,791,059 | B2 | | 7/2014 | Joichi et al. |
| 9,708,568 | B2 | | 7/2017 | Holland |
| 9,730,878 | B2 | | 8/2017 | Cetti et al. |
| 9,949,911 | B2 | | 4/2018 | Cetti |
| 2004/0156742 | A1 | | 8/2004 | Milan et al. |
| 2005/0245407 | A1 | | 11/2005 | Ishihara et al. |
| 2006/0127996 | A1 | | 6/2006 | Fahey |
| 2007/0275866 | A1 | * | 11/2007 | Dykstra ................ 510/101 |

(Continued)

FOREIGN PATENT DOCUMENTS

| EP | 0 483 426 A1 | 5/1992 |
| EP | 0 816 322 B1 | 1/1998 |

(Continued)

OTHER PUBLICATIONS

U.S. Appl. No. 61/988,912, filed May 6, 2014, Makins Holland.

(Continued)

Primary Examiner — David J Blanchard
Assistant Examiner — Sarah J Chickos
(74) Attorney, Agent, or Firm — Kathleen Y. Carter

(57) ABSTRACT

The present application relates to antiperspirant compositions comprising perfumes and sulfur-based perfume raw materials, and methods for making and using the antiperspirant compositions.

17 Claims, No Drawings

(56) References Cited

U.S. PATENT DOCUMENTS

| | | |
|---|---|---|
| 2009/0324660 A1 | 12/2009 | Cetti et al. |
| 2012/0121677 A1 | 5/2012 | Franklin |
| 2014/0170101 A1 | 6/2014 | Cetti et al. |
| 2014/0170102 A1 | 6/2014 | Kinsey et al. |
| 2014/0170194 A1 | 6/2014 | Cetti et al. |
| 2014/0179722 A1 | 6/2014 | Cetti et al. |
| 2014/0179748 A1 | 6/2014 | Cetti et al. |
| 2015/0322376 A1 | 11/2015 | Holland |
| 2017/0267944 A1 | 9/2017 | Holland |
| 2017/0312204 A1 | 11/2017 | Cetti |
| 2018/0207074 A1 | 7/2018 | Cetti |

FOREIGN PATENT DOCUMENTS

| | | |
|---|---|---|
| JP | H04-255796 A | 9/1992 |
| JP | 2005-170811 A | 6/2005 |
| WO | 2008/149065 A1 | 12/2008 |
| WO | 2010/031657 A2 | 3/2010 |

OTHER PUBLICATIONS

"The nature and duration of adaptation following long-term odor exposure", Perception & Psychophysics 1996, 58(5), 781-792.
International Search Report and Written Opinion of the International Searching Authority PCT/US2013/074886 dated Jun. 4, 2014, 26 pages.

\* cited by examiner

ANTIPERSPIRANT AND DEODORANT COMPOSITIONS

TECHNICAL FIELD

The present disclosure generally relates to antiperspirant and deodorant compositions comprising perfumes and sulfur-based perfume raw materials, as well as methods for making and using such antiperspirant and deodorant compositions that resist consumer fragrance habituation.

BACKGROUND

Consumers desire antiperspirant and deodorant compositions that provide a desired and long-lasting fragrance or scent each time the composition is applied or used. Particularly in the case of deodorants, consumers may also expect compositions that provide a scent that can mask or override other undesirable odors. While current antiperspirant and deodorant compositions provide desirable scents, consumers become habituated to the perfume raw materials (PRMs) and perfumes utilized in the existing compositions. As a result, for consumers to perceive the desired scent consumers can use increasingly large amounts of the product to overcome the habituation or the consumer can to switch to a different product utilizing a different perfume for a significant period of time to reverse the habituation. There is, therefore, a need for antiperspirant and deodorant compositions that provide long-lasting and desirable scents that do not cause a habituation effect in consumers and do not require consumers to modify their habits.

SUMMARY

In one example, an antiperspirant composition includes a perfume. The perfume includes, based on total perfume weight, from about 0.000001% to about 10% of a perfume raw material. The perfume raw material includes a sulfur atom. The perfume raw material resists the fragrance habituation of a consumer to the antiperspirant composition.

In one example, an antiperspirant composition includes a perfume. The perfume comprising, based on total perfume weight, a perfume raw material. The perfume raw material is selected from the group consisting of: (a) from about 0.0000001% to about 10%, of a perfume raw material comprising a thiol moiety; (b) from about 0.0000001% to about 10%, of a perfume raw material comprising a sulfide moiety; (c) from about 0.0000001% to about 10%, of a perfume raw material comprising a thiazole moiety; (d) from about 0.0000001% to about 10%, of a perfume raw material comprising an oxathiane moiety; (e) from about 0.00000005% to about 5%, of a perfume raw material comprising an isothiocyanate; (f) from about 0.000001% to about 10%, of a perfume raw material comprising a oxygen, sulfur, and nitrogen; and (g) mixtures thereof. The perfume raw material resists the fragrance habituation of a consumer to the antiperspirant composition.

In one example, a method of resisting the fragrance habituation of an antiperspirant composition is provided. The method includes forming an antiperspirant composition having a perfume. The perfume includes, based on total perfume weight, a perfume raw material. The perfume raw material is selected from the group consisting of: (a) from about 0.0000001% to about 10%, of a perfume raw material comprising a thiol moiety; (b) from about 0.0000001% to about 10%, of a perfume raw material comprising a sulfide moiety; (c) from about 0.0000001% to about 10%, of a perfume raw material comprising a thiazole moiety; (d) from about 0.0000001% to about 10%, of a perfume raw material comprising a oxathiane moiety; (e) from about 0.00000005% to about 5%, of a perfume raw material comprising an isothiocyanate; (f) from about 0.000001% to about 10%, of a perfume raw material comprising a sulfur, oxygen and nitrogen; and (g) mixtures thereof.

DETAILED DESCRIPTION

This application claims priority to U.S. provisional application No. 61/737,257 filed Dec. 14, 2012; U.S. provisional application No. 61/869,241 filed Aug. 23, 2013; and U.S. provisional application No. 61/879,217; all of which are incorporated herein by reference.

I. Definitions

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa.

The term "habituating" or "habituation" refers an individual or group who has decreased sensitivity to perceiving a fragrance or fragrance material. A fragrance or fragrance material is considered habituating when their Degree of Habituation (percent change in odor detection threshold or "ODT") is greater than 150%, greater than 300%, greater than 500%, greater than 1000% according to the method described in the Test Methods section of this specification.

The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to about 2% or less, about 1% or less, or about 0.1% or less of a stated ingredient. "Free of" refers to no detectable amount of the stated ingredient or thing.

II. Perfumes

Antiperspirant compositions can include perfume materials. Many consumers prefer antiperspirant compositions that can consistently provide a desired scent, or odor, that can be perceived each time the product is used. Perfume materials can provide the desired scent or odor to these antiperspirant compositions. These perfume (i.e., fragrance) materials can include perfumes, perfume raw materials, and perfume delivery systems. Habituation of the perfume materials by the consumer, however, can lead to a diminished perception of the desired scent even when the quantity of perfume material in the antiperspirant composition remains consistent.

While not being bound by theory, it is believed that habituation is a physiological phenomenon where the body is attempting to avoid having its sense of smell from becoming overwhelmed by any one stimulus after repeated chronic exposure as part of a primal, darwanistic, defense mechanism. Applicants, therefore, theorizing that the source of the habituation problem was evolutionary in nature, looked to odors that may be associated with danger as Applicants believed that the evolutionary path of those who became habituated to such odors would have been cut short. Surprisingly, it was discovered that certain chemical moieties that are associated with conditions that may be detrimental to, or important in sustaining life, are not subject to the habituation phenomenon. Antiperspirant compositions can resist scent habitation by incorporating these chemical moieties as either perfume raw materials or as components in a perfume delivery system.

In one example, an antiperspirant or deodorant composition can incorporate a perfume that can resist scent habituation. The perfume can incorporate perfume raw materials that can resist the habituation effect. The perfume raw material can include a thiol moiety, a sulfide moiety, a thiazole moiety, an oxathiane moiety, an isothiocyanate, and compounds comprising oxygen, sulfur, and nitrogen. The perfume raw materials can also be a mixture of these groups.

The quantity of perfume raw materials incorporated in a base perfume can vary. In one example, as a weight percentage of the total perfume, a thiol moiety can range from about 0.0000001% to about 10%, a sulfide moiety can range from about 0.0000001% to about 10%, a thiazole moiety can range from about 0.000001% to about 10%, an oxathiane moiety can range from 0.0000001% to about 10%, an isothiocyanate can range from about 0.00000005% to about 5%, and the compounds comprising oxygen, sulfur, and nitrogen can range from about 0.000001% to about 10%.

In another example, as a weight percentage of the total perfume, the thiol moiety can range from about 0.000001% to about 5%, the sulfide moiety can range from about 0.0000001% to about 5%, the thiazole moiety can range from about 0.000005% to about 5%, the oxathiane moiety can range from 0.000001% to about 5%, the isothiocyanate can range from about 0.0000001% to about 2.5%, and the compounds comprising oxygen, sulfur, and nitrogen can range from about 0.000005% to about 5%.

In another example, as a weight percentage of the total perfume, the thiol moiety can range from about 0.000005% to about 2.5%, the sulfide moiety can range from about 0.000005% to about 2.5%, the thiazole moiety can range from about 0.00001% to about 2.5%, the oxathiane moiety can range from about 0.000005% to about 2.5%, the isothiocyanate can range from about 0.0000005% to about 2%, and the compounds comprising oxygen, sulfur, and nitrogen can range from about 0.00001% to about 2.5%.

In another example, as a weight percentage of the total perfume, the thiol moiety can range from about 0.00001% to about 1%, the sulfide moiety can range from about 0.00001% to about 1%, the thiazole moiety can range from about 0.0005% to about 1%, the oxathiane moiety can range from about 0.00001% to about 1%, the isothiocyanate can range from about 0.000001% to about 1%, and the compounds comprising oxygen, sulfur, and nitrogen can range from about 0.0005% to about 1%.

In another example, as a weight percentage of the total perfume, the thiol moiety can range from about 0.000025% to about 0.8%, the sulfide moiety can range from about 0.000025% to about 0.5%, the thiazole moiety can range from about 0.001% to about 0.1%, the oxathiane moiety can range from about 0.000025% to about 0.8%, the isothiocyanate can range from about 0.000005% to about 0.5%, and the compounds comprising oxygen, sulfur, and nitrogen can range from about 0.001% to about 0.1%.

Certain perfume raw materials can be incorporated into a base perfume to resist the habituating effect inherent to the base perfume. As a non-limiting example, compounds having a thiol moiety can include 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; methanethiol; ethanethiol; prop-2-ene-1-thiol; propane-2-thiol; 2-methylpropane-2-thiol; propane-1-thiol; butane-2-thiol; butane-1-thiol; 2-methylpropane-1-thiol; methyldisulfanylmethane; 2-methylbutane-2-thiol; 3-methylbutane-2-thiol; 3-methylbutane-2-thiol; pentane-2-thiol; pentane-1-thiol; 2-methylbutane-1-thiol; cyclopentanethiol; 3-methyldisulfanylprop-1-ene; methylsulfanyldisulfanylmethane; 1-methyldisulfanylpropane; ethane-1,2-dithiol; 1-(methyldisulfanyl)prop-1-ene; 3-sulfanylbutan-2-one; ethyldisulfanylethane; hexane-1-thiol; 1-ethyldisulfanylpropane; thiophene-2-thiol; propane-1,3-dithiol; 3-sulfanylpentan-2-one; 2-propan-2-yldisulfanylpropane; butane-1,4-dithiol; benzenethiol; ethylsulfanyldisulfanylethane; 3-methylsulfanyldisulfanylprop-1-ene; 1-methylsulfanyldisulfanylpropane; butane-2,3-dithiol; 4-methyl-4-sulfanylpentan-2-one; 3-prop-2-enyldisulfanylprop-1-ene; 1-methoxyhexane-3-thiol; ethyl 2-sulfanylpropanoate; 1-(prop-2-enyldisulfanyl)propane; 1-propyldisulfanylpropane; 1-(4-hydroxy-3-methoxyphenyl)ethanone butane-1,3-dithiol; 1-propyldisulfanylprop-1-ene; 2-methylbenzenethiol; thiophen-2-ylmethanethiol; 3-sulfanylbutan-2-ol; phenylmethanethiolpentane-1,5-dithiol; 2-ethylbenzenethiol; 3-prop-2-enylsulfanyldisulfanylprop-1-ene; methyldisulfanyldisulfanylmethane; 1-propylsulfanyldisulfanylpropane; 2,7,7-trimethylbicyclo[3.1.1]heptane-2-thiol; 2,6-dimethylbenzenethiol; 2-phenylethanethiol; hexane-1,6-dithiol; 2-(methyldisulfanylmethyl)furan; pyridin-2-ylmethanethiol; 2-methoxybenzenethiol; (7,7-dimethyl-2-bicyclo[3.1.1]heptanyl)methanethiol; methyldisulfanylbenzene; 1-butyldisulfanylbutane; (4-methoxyphenyl)methanethiol; 2-sulfanylpropanoic acid; ethyl 2-methyldisulfanylpropanoate; (2E)-3,7-dimethylocta-2,6-diene-1-thiol; 3,7-dimethylocta-2,6-diene-1-thiol; pyrazin-2-ylmethanethiol; methyldisulfanylmethylbenzene; 2-methyl-5-(1-sulfanylpropan-2-yl)cyclohexane-1-thiol; octane-1,8-dithiol; 2-pyrazin-2-ylethanethiol; naphthalene-2-thiol; 2-oxo-3-sulfanylpropanoic acid; 2-thiophen-2-yldisulfanylthiophene; cyclohexyldisulfanylcyclohexane; 2-(furan-2-ylmethyldisulfanylmethyl)furan; phenyldisulfanylbenzene; benzyldisulfanylmethylbenzene; 8-Hydroxy-5-quinolinesulfonic acid; bis(3-methylbutyl) 2-sulfanylbutanedioate; 2-aminoethanesulfonic acid; 2-phenyl-3H-benzimidazole-5-sulfonic acid; and 2-methyl-2-sulfanylpentan-1-ol.

Non-limiting examples of compounds having a sulfide moiety can include 1-butylsulfanylbutane; ethyl 3-methylsulfanylpropanoate; 2-(methylsulfanylmethyl)furan; methylsulfanylmethane; methylsulfanylethane; 3-methylsulfanylprop-1-ene; S-methyl ethanethioate; ethylsulfanylethane; 1-methylsulfanylpropane; S-ethyl ethanethioate; 1-methylsulfanylbutane; 2-propan-2-ylsulfanylpropane; bis(methylsulfanyl)methane; 1-ethylsulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methylsulfanylacetate; S-prop-2-enyl propanethioate; 1-methylsulfanylbutan-2-one; 4-methylsulfanylbutan-2-one; 3-methylsulfanylpropan-1-am; 2,4,6-trimethyl-1,3,5-trithiane; 3-methylsulfanylbutanal; 2-methyl-1,3-thiazolidine; 2-methyl-4,5-dihydro-1,3- thiazole; ethyl 2-methylsulfanylacetate; methyl 3-methylsulfanylpropanoate; S-propan-2-yl 3-methylbutanethioate; 4-methyl-4-methylsulfanylpentan-2-one; 2-methyl-1,3-dithiolane; methyl 2-methylsulfanylbutanoate; S-methyl furan-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl)methanethioate; 1,2,4-trithiolane; 2-methylthiolan-3-one; 4-methylsulfanylbutan-1-ol; S-butan-2-yl 3-methylbutanethioate; S-butan-2-yl 3-methylbut-2-enethioate; S-(furan-2-ylmethyl)ethanethioate; 2-propyl-1,3-thiazolidine; 3-methyl-1,1-bis(methylsulfanyl)butane; 3-ethylsulfanylpropan-1-ol; S-methyl benzenecarbothioate; 3,5-dimethyl-1,2,4-trithiolane; S-butan-2-yl 2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl)propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl)ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methylsulfanylhexan-1-ol; 2-methyl-4,5-dihydrofuran-3-thiol acetate; 4-(3-oxobutylsulfanyl)butan-2-one; 3-methylsulfanylbutanoic acid; 2-methylsulfanylpyrazine; 2-methyl-3-methylsulfanylpyrazine; 2-(furan-2-ylmethylsulfanylmethyl)furan; 2-(methylsulfanylmethyl)pyrazine; 3,5-di(propan-2-yl)-1,2,4-trithiolane; 2-methylsulfanylphenol; 2-methyl-3-methylsulfanylpyrazine; ethyl 3-(furan-2-ylmethylsulfanyl)propanoate; 2,2,4,4,6,6-hexamethyl-1,3,5-trithiane; 2-methyl-5,7-dihydrothieno[3,4-d]pyrimidine; 2-amino-4-methylsulfanylbutanoic acid; (2S)-2-amino-4-methylsulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; and methyl 2-thiofuroate.

Non-limiting examples of compounds having a thiazole moiety can include 2-(2-methylpropyl)-1,3-thiazole; 2-(4-methyl-1,3-thiazol-5-yl)ethanol; 4-methyl-2-propan-2-yl-1,3-thiazole; 1-(1,3-thiazol-2-yl)ethanone; 2,4,5-Trimethylthiazole; 2-isopropyl-4-methylthiazole; 4-vinyl-5-methylthiazole; 2,4-Dimethyl-5-acetylthiazole 1,3-thiazole; 4-methyl-1,3-thiazole; 2,4-dimethyl-1,3-thiazole; 4,5-dimethyl-1,3-thiazole; 2,5-dimethyl-1,3-thiazole; 5-ethenyl-4-methyl-1,3-thiazole; 2-ethyl-4-methyl-1,3-thiazole; 4-ethyl-2-methyl-1,3-thiazole; 2-propyl-1,3-thiazole; 2,4,5-trimethyl-1,3-thiazole; 2-ethyl-1,3-thiazole; 2-ethoxy-1,3-thiazole; 2-butan-2-yl-1,3-thiazole; 5-methoxy-2-methyl-1,3-thiazole; 2-ethyl-4,5-dimethyl-1,3-thiazole; 1,3-benzothiazole; 2,5-diethyl-4-methyl-1,3-thiazole; 1-(1,3-thiazol-2-yl)propan-1-one; 4,5-dimethyl-2-(2-methylpropyl)-1,3-thiazole; 2-methyl-1,3-benzothiazole; 1-(2,4-dimethyl-1,3-thiazol-5-yl)ethanone; and 4-methyl-2-propan-2-yl-1,3-thiazole.

Non-limiting examples of compounds having an oxathiane moiety can include (2R,4S)-2-methyl-4-propyl-1,3-oxathiane, 2-methyl-4-propyl-1,3-oxathiane, and 2-pentyl-4-propyl-1,3-oxathiane.

Non-limiting examples of the compounds containing oxygen, sulfur, and nitrogen include 2-(4-methyl-1,3-thiazol-5-yl)ethanol; 1-(1,3-thiazol-2-yl)ethanone; 6-methyl-7-Oxa-1-thia-4-azaspiro[4.4]nonane; 2-[(furan-2-ylmethyl)sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3-thiazol-2-yl)ethanone; 1-(1,3-thiazol-2-yl)propan-1-one; 1-(2,4-dimethyl-1,3-thiazol-5-yl)ethanone; 2-amino-4-methylsulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid.

More specific examples of the thiol moiety can include a-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; and 4-methoxy-2-methylbutane-2-thiol.

More specific examples of the sulfide moiety can include 1-butylsulfanylbutane; ethyl 3-methylsulfanylpropanoate; and 2-(methylsulfanylmethyl)furan.

More specific examples of compounds having a thiazole moiety can include 2-(2-methylpropyl)-1,3-thiazole; 2-(4-methyl-1,3-thiazol-5-yl)ethanol; 4-methyl-2-propan-2-yl-1,3-thiazole; 4-methyl-2-propan-2-yl-1,3-thiazole; and 1-(1,3-thiazol-2-yl)ethanone.

A more specific example of compounds having an oxathiane moiety can be (2R,4S)-2-methyl-4-propyl-1,3-oxathiane.

More specific examples of a compound comprising oxygen, sulfur, and nitrogen can include 2-(4-methyl-1,3-thiazol-5-yl)ethanol, 1-(1,3-thiazol-2-yl)ethanone; and 6-methyl-7-Oxa-1-thia-4-azaspiro[4.4]nonane.

In another example, the perfume raw materials can include sulfide moieties or thiazole moieties. The sulfide moieties can include 1-butylsulfanylbutane, 4,7,7-trimethyl-6-thiabicyclo[3.2.1]octane, and 2-methyl-3-methylsulfanylpyrazine. The thiazole moieties can include 1-(1,3-thiazol-2-yl)ethanone.

In another example, the perfume raw materials can be added to the base perfume in a group. Suitable groups can include group (a): 1-butylsulfanylbutane; (2R,4S)-2-methyl-4-propyl-1,3-oxathiane; and 4-methoxy-2-methylbutane-2-thiol; group (b): 2-(4-methyl-1,3-thiazol-5-yl)ethanol; 7-Oxa-1-thia-4-azaspiro[4.4]nonane; and 6-methyl-, 1-(1,3-thiazol-2-yl)ethanone; group (c): 2-(methylsulfanylmethyl)furan; ethyl 3-methylsulfanylpropanoate; and 1-butylsulfanylbutane; group (d): 5-methyl-5-sulfanylhexan-3-one; 5-methyl-2-(2-sulfanylpropan-2-yl)cyclohexan-1-one; and 2-(4-methyl-1-cyclohex-3-enyl)propane-2-thiol; group (e): 2-(2-methylpropyl)-1,3-thiazole; 2-(4-methyl-1,3-thiazol-5-yl)ethanol; and 4-methyl-2-propan-2-yl-1,3-thiazole; and group (f): (2R,4S)-2-methyl-4-propyl-1,3-oxathiane; 2-(4-methyl-1-cyclohex-3-enyl)propane-2-thiol; and (NE)-N-[(6E)-2,4,4,7-tetramethylnona-6,8-dien-3-ylidene]hydroxylamine.

Examples of some formulated habituation-resistant perfumes suitable for incorporation into antiperspirant compositions are disclosed in Table 1. The perfumes in Table 1 include thiol and oxathiane sulfur-based moieties in the grapefruit zest #925 and castech compounds respectively. Additionally, a nitrogen-based habituation reducing oxime group is included in the labienoxime compound.

TABLE 1

| Perfume Raw Material | Perfume A | Perfume B | Perfume C | Perfume D | Perfume E | Perfume F | Perfume G |
|---|---|---|---|---|---|---|---|
| 4-Tertiary Butyl Cyclohexyl Acetate | 2.50% | 2.50% | 3.00% | 3.00% | 3.50% | 3.50% | 3.50% |

TABLE 1-continued

| Perfume Raw Material | Perfume A | Perfume B | Perfume C | Perfume D | Perfume E | Perfume F | Perfume G |
|---|---|---|---|---|---|---|---|
| Allyl Caproate | 0.20% | 0.10% | 0.10% | 0.20% | 0.10% | 0.20% | 0.20% |
| Allyl Cyclohexane Propionate | 1.25% | 2.00% | 1.25% | 2.00% | 2.00% | 2.00% | 2.00% |
| Allyl Heptoate | 3.50% | 2.90% | 3.50% | 3.50% | 4.00% | 3.00% | 3.00% |
| Benzyl Acetate | 3.00% | 3.00% | 3.00% | 2.00% | 2.00% | 2.00% | 3.00% |
| Benzyl Salicylate | 5.00% | 5.00% | 5.00% | 5.00% | 5.00% | 5.00% | 5.00% |
| Beta Gamma Hexenol | 0.20% | 0.15% | 0.10% | 0.20% | 0.15% | 0.10% | 0.20% |
| Castech | 1.00% | 0.90% | 1.00% | 0.95% | 1.25% | 0.90% | 0.85% |
| Cis 3 Hexenyl Acetate | 0.10% | 0.20% | 0.10% | 0.10% | 0.20% | 0.10% | 0.10% |
| Cis Jasmone | 0.10% | 0.10% | 0.10% | 0.20% | 0.10% | 0.10% | 0.10% |
| Cyclopentol Hc 937165 | 0.20% | 0.20% | 0.40% | 0.40% | 0.20% | 0.40% | 0.40% |
| Delta Damascone | 0.10% | 0.20% | 0.10% | 0.20% | 0.10% | 0.10% | 0.10% |
| Dihydro Iso Jasmonate | 1.00% | 1.00% | 1.25% | 0.75% | 1.50% | 1.50% | 0.79% |
| Dihydro Myrcenol | 2.50% | 3.00% | 2.50% | 2.50% | 3.00% | 3.00% | 2.00% |
| Dimethyl Benzyl Carbinyl Acetate | 4.00% | 2.00% | 5.00% | 1.00% | 3.50% | 3.00% | 2.00% |
| Dimethyl Benzyl Carbinyl Butyrate | 1.00% | 2.00% | 1.00% | 1.00% | 0.70% | 1.00% | 2.00% |
| Ethyl 2 Methyl Pentanoate | 0.20% | 0.10% | 0.15% | 0.10% | 0.15% | 0.20% | 0.40% |
| Ethyl Acetoacetate | 1.50% | 2.50% | 2.50% | 1.40% | 1.75% | 1.50% | 2.00% |
| Ethyl Butyrate | 0.10% | 0.10% | 0.25% | 0.25% | 0.20% | 0.20% | 0.10% |
| Ethyl Caproate FCC | 0.50% | 0.40% | 0.40% | 0.50% | 0.50% | 0.50% | 0.50% |
| Ethyl Maltol | 0.75% | 0.50% | 0.75% | 0.50% | 0.50% | 1.00% | 1.00% |
| Ethyl Oenanthate | 0.50% | 0.20% | 0.15% | 0.15% | 0.20% | 0.50% | 0.40% |
| Ethyl-2-Methyl Butyrate | 0.50% | 0.75% | 0.50% | 0.50% | 0.75% | 0.75% | 0.75% |
| Ethylene Brassylate | 3.00% | 4.00% | 4.00% | 5.00% | 3.00% | 3.00% | 3.00% |
| Florhydral | 0.25% | 0.25% | 0.25% | 0.50% | 0.50% | 0.50% | 0.25% |
| Gamma Decalactone | 0.50% | 1.00% | 1.25% | 0.78% | 0.50% | 0.40% | 0.65% |
| Grapefruit Zest #925 (C-Citrus&Allied) | 0.15% | 0.30% | 0.20% | 0.25% | 0.35% | 0.35% | 0.50% |
| Hexamethylindanopyran | 10.00% | 8.00% | 8.00% | 8.00% | 8.00% | 10.00% | 10.00% |
| Hexyl Acetate | 1.25% | 1.75% | 1.75% | 1.50% | 1.00% | 0.50% | 0.50% |
| Hexyl Cinnamic Aldehyde | 7.00% | 8.50% | 10.00% | 10.00% | 5.00% | 5.00% | 7.00% |
| Indolene | 0.10% | 0.10% | 0.10% | 0.20% | 0.10% | 0.10% | 0.20% |
| Ionone Beta | 2.00% | 1.50% | 1.25% | 1.25% | 1.50% | 1.50% | 1.00% |
| Iso E Super Or Wood | 2.50% | 2.00% | 1.50% | 2.00% | 2.00% | 3.00% | 2.50% |
| Italian Mandarin Oil Yellow #10567 | 0.50% | 1.00% | 0.50% | 1.00% | 0.50% | 1.08% | 0.50% |
| Jasmal | 0.50% | 0.40% | 0.40% | 0.50% | 0.40% | 0.50% | 0.40% |
| Labienoxime 10 Opt | 0.85% | 0.75% | 0.70% | 1.00% | 0.80% | 1.00% | 0.75% |
| Ligustral Or Triplal | 0.20% | 0.20% | 0.40% | 0.25% | 0.35% | 0.35% | 0.20% |
| Linalool | 6.00% | 6.00% | 6.00% | 6.00% | 6.00% | 6.50% | 7.00% |
| Linalyl Acetate | 2.00% | 2.00% | 1.00% | 2.00% | 2.00% | 3.00% | 1.00% |
| Linalyl Benzoate | 0.50% | 1.00% | 0.40% | 0.40% | 1.00% | 0.50% | 0.50% |
| Methyl Dihydro Jasmonate | 5.00% | 5.00% | 5.00% | 5.00% | 5.00% | 5.00% | 5.00% |
| Methyl Iso Butenyl Tetrahydro Pyran | 0.05% | 0.02% | 0.02% | 0.02% | 0.05% | 0.02% | 0.01% |
| Methyl Phenyl Carbinyl Acetate | 0.68% | 0.75% | 1.50% | 1.50% | 1.00% | 1.00% | 0.60% |
| Nectaryl | 2.00% | 1.00% | 1.00% | 1.00% | 2.00% | 2.00% | 1.00% |
| Nonalactone | 0.50% | 0.50% | 0.75% | 0.25% | 0.75% | 0.20% | 0.20% |
| Oil Lemon Brazilcp Select Fcc Enh 15130 | 2.00% | 3.00% | 2.50% | 2.00% | 3.00% | 2.50% | 2.50% |
| Oil Pink Grapefruit California Fcc 15029 | 6.50% | 7.00% | 5.50% | 7.00% | 5.50% | 6.50% | 6.00% |
| Phenoxy Ethyl Iso Butyrate | 3.00% | 3.00% | 2.00% | 3.00% | 5.00% | 2.00% | 5.00% |
| Prenyl Acetate | 0.20% | 0.25% | 0.40% | 0.25% | 0.35% | 0.45% | 0.40% |
| Sandalore | 0.50% | 0.50% | 0.50% | 0.75% | 1.00% | 1.00% | 1.00% |
| Synambran R 50% In IPM | 0.22% | 0.18% | 0.18% | 0.20% | 0.40% | 0.50% | 0.20% |
| Undecalactone | 7.00% | 4.50% | 4.50% | 5.00% | 5.00% | 4.50% | 5.00% |
| Undecavertol | 0.10% | 0.50% | 0.10% | 0.50% | 0.10% | 1.00% | 0.50% |
| Veloutone | 0.25% | 0.25% | 0.25% | 0.50% | 0.50% | 0.50% | 0.25% |
| Verdox | 5.00% | 5.00% | 6.00% | 6.00% | 6.00% | 5.00% | 6.00% |
| TOTALS: | 100% | 100% | 100% | 100% | 100% | 100% | 100% |

Suitable perfume raw materials may be obtained from: Symrise GmbH, with offices located at Muhlenfeldstrasse 1, Holzminden, 37603, Germany; International Flavors & Fragrances Inc., a New York corporation having an address at 521 W 57th Street, New York, N.Y. 10019; Givaudan Suisse SA a Swiss corporation having an address at 1214 Vernier, Switzerland; Firmenich Inc., with offices located at 250 Plainsboro Rd., Plainsboro Township, N.J. 08536, United States; and Takasago International Corporation (USA), with offices located at 4 Volvo Drive, Rockleigh, N.J. 07647, United States.

Antiperspirants compositions can also incorporate desirable scents through inclusion of perfumes and perfume raw materials in perfume delivery systems. Certain perfume delivery systems, methods of making certain perfume delivery systems, and the uses of such perfume delivery systems are disclosed in U.S. Pre-Grant Publication No. 2007/0275866 A1. The perfumes and perfume raw materials previously disclosed can be used in such perfume delivery systems. Such perfume delivery systems include: polymer-assisted delivery (PAD), molecule-assisted delivery (MAD), fiber-assisted deliver (FAD), amine-assisted delivery (AAD), cyclodextrin delivery system (CD), starch encapsulated accord (SEA), inorganic carrier delivery system (ZIC), and Pro-Perfume (PP). Examples of these perfume delivery systems are further described below.

Polymer-Assisted Delivery (PAD)

This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD systems can include, but are not limited to, matrix systems, and reservoir systems.

In a matrix system, the fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology. Nano, or micro-particles, composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

A "standard" matrix system refers to systems that are "pre-loaded" with the intent of keeping the pre-loaded perfume associated with the polymer until the moment, or moments of, perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Suitable micro-particles and micro-latexes as well as methods of making same may be found in U.S. Pre-Grant Publication No. 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccharides and nanolatexes may be combined with other PDTs, including other PAD systems such as PAD reservoir systems in the form of a perfume microcapsule (PMC). Polymer Assisted Delivery (PAD) matrix systems may include those described in the following references: U.S. Pre-Grant Publication No. 2004/0110648 A1 and U.S. Pat. No. 6,531,444.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Suitable silicones as well as making same may be found in U.S. Pre-Grant Publication No. 2005/0143282 A1. Functionalized silicones may also be used as described in U.S. Pre-Grant Publication No. 2006/003913 A1. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP). Other such examples may be found in U.S. Pre-Grant Publication No. 2005/0003980 A1.

Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. Suitable capsule wall materials include, in addition to aminoplasts, polyvinyl alcohol, polyvinyl pyrrolidone, polyethylene glycol, polysaccharides and modified polysaccharides, gel forming proteins, modified celluloses such as carboxymethylcelluloses and hydroxyethylcelluloses, polyacrylates, polyureas, polyurethanes and mixtures thereof. The capsules may be further coated with an additional coating that can improve the deposition and/or retention of the capsule on the desired surface. Suitable coating materials include a cationic polymer selected from the group consisting of selected from the group consisting of polysaccharides, cationically modified starch, cationically modified guar, polysiloxanes, poly diallyl dimethyl ammonium halides, copolymers of poly diallyl dimethyl ammonium chloride and vinyl pyrrolidone, acrylamides, imidazoles, imidazolinium halides, imidazolium halides, poly vinyl amine, copolymers of poly vinyl amine and N-vinyl formamide to the surface of the capsule to form a cationically coated polymer encapsulated material. Typical capsules have a diameter of 1 micron to 500 microns. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged.

Molecule-Assisted Delivery (MAD)

Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one example, non-polymeric materials or molecules have a C Log P greater than about 2. Molecule-Assisted Delivery (MAD) may also include those described in U.S. Pat. No. 7,119,060.

Fiber-Assisted Delivery (FAD)

The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be woven and non-woven as well as natural or synthetic. Natural fibers include those produced by plants, animals, and geological processes, and include but are not limited to cellulose materials such as cotton, linen, hemp jute, flax, ramie, and sisal, and fibers used to manufacture paper and cloth. Fiber-Assisted Delivery may consist of the use of wood fiber, such as thermo-mechanical pulp and bleached or unbleached kraft or sulfite pulps. Animal fibers consist largely of particular proteins, such as silk, sinew, catgut and hair (including wool). Polymer fibers based on synthetic chemicals include but are not limited to polyamide nylon, PET or PBT polyester, phenol-formaldehyde (PF), polyvinyl alcohol fiber (PVOH), polyvinyl chloride fiber (PVC), polyolefins (PP and PE), and acrylic polymers. All such fibers may be pre-loaded with a perfume, and then added to a product that may or may not contain free perfume and/or one or more perfume delivery technologies. In one example, the fibers may be added to a product prior to being loaded with a perfume, and then loaded with a perfume by adding a perfume that may diffuse into the fiber, to the product. Without wishing to be bound by theory, the perfume may absorb onto or be adsorbed into the fiber, for example, during product storage, and then be released at one or more moments of truth or consumer touch points.

Amine-Assisted Delivery (AAD)

The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one example, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one example, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines. Without technology, volatile top notes can be lost too quickly, leaving a higher ratio of middle and base notes to top notes. The use of a polymeric amine allows higher levels of top notes and other PRMS to be used to obtain freshness longevity without causing neat product odor to be more intense than desired, or allows top notes and other PRMs to be used more efficiently. In one example, AAD systems are effective at delivering PRMs at pH greater than about neutral. Without wishing to be bound by theory, conditions in which more of the amines of the AAD system are deprotonated may result in an increased affinity of the deprotonated amines for PRMs such as aldehydes and ketones, including unsaturated ketones and enones such as damascone. In another example, polymeric amines are effective at delivering PRMs at pH less than about neutral. Without wishing to be bound by theory, conditions in which more of the amines of the AAD system are protonated may result in a decreased affinity of the protonated amines for PRMs such as aldehydes and ketones, and a strong affinity of the polymer framework for a broad range of PRMs. In such an example, polymer-assisted delivery may be delivering more of the perfume benefit; such systems are a subspecies of AAD and may be referred to as Amine-Polymer-Assisted Delivery or APAD. In some cases when the APAD is employed in a composition that has a pH of less than seven, such APAD systems may also be considered Polymer-Assisted Delivery (PAD). In yet another example, AAD and PAD systems may interact with other materials, such as anionic surfactants or polymers to form coacervate and/or coacervates-like systems. In another example, a material that contains a heteroatom other than nitrogen, for example sulfur, phosphorus or selenium, may be used as an alternative to amine compounds. In yet another example, the aforementioned alternative compounds can be used in combination with amine compounds. In yet another example, a single molecule may comprise an amine moiety and one or more of the alternative heteroatom moieties, for example, thiols, phosphines and selenols. Suitable AAD systems as well as methods of making same may be found in U.S. Pat. No. 6,103,678.

Cyclodextrin Delivery System (CD)

This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable cyclodextrin delivery systems as well as methods of making the same may be found in U.S. Pre-Grant Publication No. 2006/0263313 A1.

Starch Encapsulated Accord (SEA)

The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in U.S. Pat. No. 6,458,754 B1.

Inorganic Carrier Delivery System (ZIC)

This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Suitable zeolite and inorganic carriers as well as methods of making same may be found in U.S. Pre-Grant Publication No. 2005/0003980 A1. Silica is another form of ZIC. Another example of a suitable inorganic carrier includes inorganic tubules, where the perfume or other active material is contained within the lumen of the nano- or micro-tubules. Preferably, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

Pro-Perfume (PP)

This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include those that are monomeric (non-polymeric) or polymeric, and may be pre-formed or may be formed in-situ under equilibrium conditions, such as those that may be present during in-product storage or on the wet or dry situs.

Nonlimiting examples of pro-perfumes include Michael adducts (e.g., beta-amino ketones), aromatic or non-aromatic imines (Schiffs Bases), oxazolidines, beta-keto esters, and orthoesters. Another example includes compounds comprising one or more beta-oxy or beta-thio carbonyl moieties capable of releasing a PRM, for example, an alpha, beta-unsaturated ketone, aldehyde or carboxylic ester. The typical trigger for perfume release is exposure to water; although other triggers may include enzymes, heat, light, pH change, autoxidation, a shift of equilibrium, change in concentration or ionic strength and others. For aqueous-based products, light-triggered pro-perfumes are particularly suited. Such photo-pro-perfumes (PPPs) include but are not limited to those that release coumarin derivatives and perfumes and/or pro-perfumes upon being triggered. The released pro-perfume may release one or more PRMs by means of any of the above mentioned triggers. In one example, the photo-pro-perfume releases a nitrogen-based pro-perfume when exposed to a light and/or moisture trigger. In another example, the nitrogen-based pro-perfume, released from the photo-pro-perfume, releases one or more PRMs selected, for example, from aldehydes, ketones (including enones) and alcohols. In still another example, the PPP releases a dihydroxy coumarin derivative. The light-triggered pro-perfume may also be an ester that releases a coumarin derivative and a perfume alcohol. In one example the pro-perfume is a dimethoxybenzoin derivative as described in U.S. Pre-Grant Publication No. 2006/0020459 A1. In another example the pro-perfume is a 3',5'-dimethoxybenzoin (DMB) derivative that releases an alcohol upon exposure to electromagnetic radiation. In yet another example, the pro-perfume releases one or more low ODT PRMs, including tertiary alcohols such as linalool, tetrahydrolinalool, or dihydromyrcenol. Suitable pro-perfumes and methods of making same can be found in U.S. Pat. No. 7,018,978 B2.

An amine reaction product ("ARP") is a subclass or species of PP. One may also use "reactive" polymeric amines in which the amine functionality is pre-reacted with one or more PRMs to form an amine reaction product (ARP). Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxylamines, such as 2-aminoethanol and its alkyl substituted derivatives, and aromatic amines such as anthranilates. The ARPs may be premixed with perfume or added separately in leave-on or rinse-off applications. In another example, a material that contains a heteroatom other than nitrogen, for example oxygen, sulfur, phosphorus or selenium, may be used as an alternative to amine compounds. In yet another example, the aforementioned alternative compounds can be used in combination with amine compounds. In yet another example, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in U.S. Pat. No. 6,413,920 B1.

The perfumes disclosed herein can be used as the perfume component pro-perfume compounds that contain sulfur. The term "pro-perfume compound" herein refers to compounds resulting from the chemical bonding of perfume raw materials (PRMs) with materials that comprise sulfur. The pro-perfume compound can release the original PRM (i.e., pre-converted) upon exposure to a trigger such as water or light or atmospheric oxygen. Suitable methods of making the same can be found in U.S. Pat. No. 7,018,978.

Amounts of Perfumes and PRMs Used in Delivery Systems

In one example, the perfumes and PRM disclosed herein, including those in Table 1, and stereoisomers thereof are suitable for use, in perfume delivery systems at levels, based on total perfume delivery system weight, of from 0.001% to about 50%, from 0.005% to 30%, from 0.01% to about 10%, from 0.025% to about 5%, or even from 0.025% to about 1%.

In one example, the perfume delivery systems disclosed herein are suitable for use in antiperspirant compositions at levels, based on total antiperspirant composition weight, from about 0.001% to about 20%, from about 0.01% to about 10%, from about 0.05% to about 5%, from about 0.1% to about 0.5%.

In one example, the amount of the perfumes and PRM disclosed herein, including those Table 1 PRMs, based on the total microcapsules and/or nanocapsules (Polymer Assisted Delivery (PAD) Reservoir System) weight, may be from about 0.1% to about 99%, from 25% to about 95%, from 30 to about 90%, from 45% to about 90%, from 65% to about 90%.

In one example, the amount of total perfume based on total weight of starch encapsulates and starch agglomerates (Starch Encapsulated Accord (SEA)) ranges from 0.1% to about 99%, from 25% to about 95%, from 30 to about 90%, from 45% to about 90%, from 65% to about 90%. In one example, the perfumes and PRM disclosed herein, including those disclosed in Table 1, and stereoisomers thereof are suitable for use, in such starch encapsulates and starch agglomerates. Such perfumes, PRMs and stereoisomers thereof may be used in combination in such starch encapsulates and starch agglomerates.

In one example, the amount of total perfume based on total weight of [cyclodextrin-perfume]complexes (Cyclodextrin (CD)) ranges from 0.1% to about 99%, from 2.5% to about 75%, from 5% to about 60%, from 5% to about 50%, from 5% to about 25%. In one example, the perfumes and PRM disclosed herein, including those disclosed in Table 1, and stereoisomers thereof are suitable for use in such [cyclodextrin-perfume]complexes. Such perfumes, PRMs and stereoisomers thereof may be used in combination in such [cyclodextrin-perfume]complexes.

In one example, the amount of total perfume based on total weight of Polymer Assisted Delivery (PAD) Matrix Systems (including Silicones) ranges from 0.1% to about 99%, from 2.5% to about 75%, from 5% to about 60%, from 5% to about 50%, from 5% to about 25%. In one example, the amount of total perfume based on total weight of a hot melt perfume delivery system/perfume loaded plastic Matrix System and ranges from 1% to about 99%, from 2.5% to about 75%, from 5% to about 60%, from 5% to about 50%, from 10% to about 50%. In one example, the perfumes and PRM disclosed herein, including those disclosed in Table 1, and stereoisomers thereof, are suitable for use, in such Polymer Assisted Delivery (PAD) Matrix Systems, including hot melt perfume delivery system/perfume loaded plastic Matrix Systems. Such perfumes, PRMs and stereoisomers thereof may be used in combination in such Polymer Assisted Delivery (PAD) Matrix Systems (including hot melt perfume delivery system/perfume loaded plastic Matrix Systems).

In one example, the amount of total perfume based on total weight of Amine Assisted Delivery (AAD) (including Aminosilicones) ranges from 1% to about 99%, from 2.5% to about 75%, from 5% to about 60%, from 5% to about 50%, from 5% to about 25%. In one example, the perfumes and PRM disclosed herein, including those disclosed in Table 1, and stereoisomers thereof are suitable for use, in such Amine Assisted Delivery (AAD) systems.

In one example, the amount of total perfume based on total weight of Pro-Perfume (PP) Amine Reaction Product (ARP) system ranges from 0.1% to about 99%, from about 1% to about 99%, from 5% to about 90%, from 10% to about 75%, from 20% to about 75%, from 25% to about 60%. In one example, the perfumes and PRM disclosed herein, including those disclosed in Table 1, and stereoisomers thereof are suitable for use, in such Pro-Perfume (PP) Amine Reaction Product (ARP) systems.

III. Antiperspirant Compositions

Antiperspirant compositions can be formulated in many forms. For example an antiperspirant composition can be, without limitation, a roll on product, a body spray, a stick including soft solid sticks and invisible solids, or an aerosol. Each form can include the perfume materials to create an antiperspirant composition that can resist or eliminate habituation to the provided scent. Each of the antiperspirant compositions described below can include perfume materials as described herein.

A. Roll-on and Clear Gel

A roll-on antiperspirant composition can comprise, for example, water, emollient, solubilizer, deodorant actives, antioxidants, preservatives, or combinations thereof. A clear gel antiperspirant composition can comprise, for example, water, emollient, solubilizer, deodorant actives, antioxidants, preservatives, ethanol, or combinations thereof.

Water

The roll-on composition can include water. Water can be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the deodorant composition.

Emollients

Roll-on compositions can comprise an emollient system including at least one emollient, but it could also be a combination of emollients. Suitable emollients are often liquid under ambient conditions. Depending on the type of product form desired, concentrations of the emollient(s) in the deodorant compositions can range from about 1% to about 95%, from about 5% to about 95%, from about 15% to about 75%, from about 1% to about 10%, from about 15% to about 45%, or from about 1% to about 30%, by weight of the deodorant composition.

Emollients suitable for use in the roll-on compositions include, but are not limited to, propylene glycol, polypropylene glycol (like dipropylene glycol, tripropylene glycol, etc.), diethylene glycol, triethylene glycol, PEG-4, PEG-8, 1,2 pentanediol, 1,2 hexanediol, hexylene glycol, glycerin, C2 to C20 monohydric alcohols, C2 to C40 dihydric or polyhydric alcohols, alkyl ethers of polyhydric and monohydric alcohols, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Deodorant Actives

Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. The concentration of the optional deodorant active may range from about 0.001%, from about 0.01%, of from about 0.1%, by weight of the composition to about 20%, to about 10%, to about 5%, or to about 1%, by weight of the composition.

Odor Entrappers

The composition can include an odor entrapper. Suitable odor entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

Buffering Agent

The composition can include a buffering agent which may be alkaline, acidic or neutral. The buffer can be used in the composition for maintaining the desired pH. The composition may have a pH from about 3 to about 10, from about 4 to about 9, from about 5 to about 8, from about 6 to about 7, or it may have a pH of about 6.5. One unique feature of the polyvinyl amine malodor control polymers is its ability to maintain active nitrogen sites at high pH levels which can help enhance the antibacterial effect which comes, at least in part, from the nitrogen sites.

Suitable buffering agents include, for example, hydrochloric acid, sodium hydroxide, potassium hydroxide, and combinations thereof.

The compositions can contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer

The composition can contain a solubilizer. A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof.

Suitable solubilizers include, for example, hydrogenated castor oil, polyoxyethylene 2 stearyl ether, polyoxyethylene 20 stearyl ether, and combinations thereof. One suitable hydrogenated castor oil that may be used in the present composition is polyoxyethylene hydrogenated castor oil.

When the solubilizing agent is present, it is typically present at a level of from about 0.01% to about 5%, alternatively from about 0.01% to about 3%, alternatively from about 0.05% to about 1%, alternatively from about 0.01% to about 0.05%, by weight of the composition.

Preservatives

The composition can include a preservative. The preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl)urea, commonly known as diazolidinyl urea, available under the trade name Germall® II from Sutton Laboratories, Inc.; N,N''-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koral-one™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

B. Body Spray

A body spray can contain, for example, a carrier, perfume, a deodorant active, odor entrappers, propellant, or combinations thereof. The body spray compositions can be applied as a liquid.

Carrier

A carrier suitable for use in a body spray can include, water, alcohol, or combinations thereof. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. A suitable example of an alcohol can include ethanol.

Propellant

The compositions described herein can include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoro-ethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 difluoroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42%, or any combination thereof, by weight of the total fill of materials stored within the container.

C. Invisible Solid

Invisible solid antiperspirant compositions as described herein can contain a primary structurant, an antiperspirant active, a perfume, and additional chassis ingredient(s). The antiperspirant composition can further comprise other optional ingredient(s). The compositions can be in the form of a solid stick. The compositions can have a product hardness of about 600 gram force or more. The compositions may be free of dipropylene glycol, added water, castor wax, or any combination thereof. The antiperspirant composition may be anhydrous. The antiperspirant composition may be free of added water.

Hardness

The invisible solid can have a product hardness of least about 600 gram·force, more specifically from about 600 gram·force to about 5,000 gram·force, still more specifically from about 750 gram·force to about 2,000 gram·force, and yet more specifically from about 800 gram·force to about 1,400 gram·force.

The term "product hardness" or "hardness" as used herein is a reflection of how much force is required to move a penetration cone a specified distance and at a controlled rate into an antiperspirant composition under the test conditions described herein below. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Primary Structurants

The invisible solid can comprise a suitable concentration of a primary structurant to help provide the antiperspirant with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the antiperspirant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Other non-limiting examples of primary structurants suitable for use herein are described in U.S. Pat. Nos. 5,976,514 and 5,891,424, the descriptions of which are incorporated herein by reference.

Antiperspirant Active

The antiperspirant stick compositions can comprise a particulate antiperspirant active suitable for application to human skin. The concentration of antiperspirant active in the composition should be sufficient to provide the desired perspiration wetness and odor control from the antiperspirant stick formulation selected.

The antiperspirant stick compositions can comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about 10 microns.

The antiperspirant active for use in the anhydrous antiperspirant compositions of the present invention can include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_aCl_b\cdot xH_2O,$$

wherein a is from about 2 to about 5;
the sum of a and b is about 6;
x is from about 1 to about 6; and
a, b, and x may have non-integer values.

More specifically, aluminum chlorohydroxides referred to as "5/6 basic chlorohydroxide" can be used, wherein a=5, and "2/3 basic chlorohydroxide", wherein a=4.

Processes for preparing aluminum salts are disclosed in U.S. Pat. Nos. 3,887,692; 3,904,741; 4,359,456; and British Patent Specification 2,048,229, the disclosures of which are incorporated herein by reference for the purpose of describing processes for preparing aluminum salts.

Mixtures of aluminum salts are described in British Patent Specification 1,347,950, which description is also incorporated herein by reference.

Zirconium salts for use in the anhydrous antiperspirant stick compositions include those which conform to the formula:

$$ZrO(OH)_{2-a}Cl_a\cdot xH_2O,$$

wherein a is from about 1.5 to about 1.87;
x is from about 1 to about 7; and
a and x may both have non-integer values.

These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068; Great Britain Patent Application 2,144,992; and U.S. Pat. No. 4,120,948, disclosures of which are incorporated herein by reference for the limited purpose of describing ZAG complexes.

Also suitable for use herein are enhanced efficacy aluminum-zirconium chlorohydrex-amino acid which typically has the empirical formula $Al_nZr(OH)_{[3n+4-m(n+1)]}(Cl)_{[m(n+1)]}$-AAq where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, 3-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

Additional Chassis Ingredients

Additional Structurant

The antiperspirant composition can further comprise an additional structurant. The additional structurant may be present in an amount from 1% to about 10%, by weight of the composition. The additional structurant(s) will likely be present at an amount less than the primary structurant.

Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof.

Other non-limiting examples of additional structurants suitable for use herein are described in U.S. Pat. Nos. 5,976,514 and 5,891,424.

Solvent

The antiperspirant composition can comprise a solvent at concentrations ranging from about 20% to about 80%, and more specifically from about 30% to about 70%, by weight of the composition. The solvent can be a volatile silicone which may be cyclic or linear.

"Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference.

The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C.

Linear volatile silicone materials suitable for use in the antiperspirant compositions include those represented by the formula:

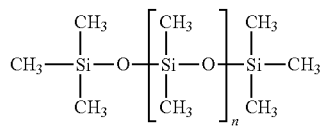

wherein n is from 1 to 7, and more specifically from 2 to 3. These linear silicone materials will generally have viscosities of less than about 5 centistokes at 25° C.

Specific examples of volatile silicone solvents suitable for use in the antiperspirant compositions include, but are not limited to, Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids

Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Other Optional Ingredients

The anhydrous antiperspirant compositions can further comprise any optional material that is known for use in antiperspirant and deodorant compositions or other personal care products, or which is otherwise suitable for topical application to human skin.

One example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, and so forth. Examples of such optional materials are described in U.S. Pat. Nos. 4,049,792; 5,019,375; and 5,429,816; which descriptions are incorporated herein by reference.

D. Soft Solid

Soft solid composition can comprise volatile silicone, antiperspirant active, gellant, residue masking material, or combinations thereof. In addition, soft solids generally have a hardness value after dispensing of about 500 gram force or less.

Volatile Silicone Solvent

The soft solid can comprises a volatile silicone solvent at concentrations ranging from about 20% to about 80%, preferably from about 30% to about 70%, more preferably from about 45% to about 70%, by weight of the composition. The volatile silicone of the solvent may be cyclic or linear.

"Volatile silicone" as used herein refers to those silicone materials which have measurable vapor pressure under ambient conditions. Nonlimiting examples of suitable volatile silicones are described in Todd et al., "Volatile Silicone Fluids for Cosmetics", Cosmetics and Toiletries, 91:27-32 (1976), which descriptions are incorporated herein by reference. Preferred volatile silicone materials are those having from about 3 to about 7, preferably from about 4 to about 5, silicon atoms.

Cyclic volatile silicones are preferred for use in the antiperspirant compositions herein, and include those represented by the formula:

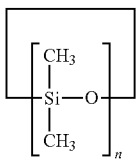

wherein n is from about 3 to about 7, preferably from about 4 to about 5, most preferably 5.

These cyclic silicone materials will generally have viscosities of less than about 10 centistokes at 25° C.

Linear volatile silicone materials suitable for use in the antiperspirant compositions include those represented by the formula:

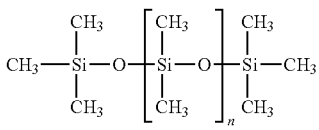

wherein n is from about 1 to about 7, preferably from about 2 to about 3. These linear silicone materials will generally have viscosities of less than about 5 centistokes at 25° C.

Specific examples of volatile silicone solvents suitable for use in the antiperspirant compositions include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicones Corp.).

Gellant Material

The soft solid can include a gellant material comprising fatty alcohols having from about 20 to about 60 carbon atoms, or combinations thereof, at concentrations ranging from about 0.1% to about 8% by weight of the composition. The gellant material, when combined with the volatile silicone solvent described hereinbefore, provides the composition with a physically stable structure within which the particulate antiperspirant materials are dispersed, and maintained as such over an extended period of time.

Specifically, the gellant material can comprise saturated or unsaturated, substituted or unsubstituted, fatty alcohols or mixtures of fatty alcohols having from about 20 to about 60 carbons atoms, preferably from about 20 to about 40 carbon atoms. Preferred are combinations of the fatty alcohols. The fatty alcohol gellants are preferably saturated, unsubstituted monohydric alcohols or combinations thereof, which have a melting point of at less than about 110° C., more preferably from about 60° to about 110° C., even more preferably between about 100° C. and 110° C.

It has been found that this fatty alcohol-based gellant material, when combined with volatile silicone solvents provides a stable structure for maintaining a dispersion of particulate antiperspirant material in a topical formulation without the necessity of using conventional particulate thickening agents. This gellant material is especially useful in maintaining the physical stability of particulate dispersions containing higher concentrations of volatile silicone solvents.

It was also found that penetration force values for the antiperspirant compositions can be controlled by adjusting total fatty alcohol concentrations. In controlling penetration force values in this manner, there is no longer a need to use organic solvents or thickening agents to control penetration force values, which solvents or thickening agents often add cost to the formulation, introduce additional compatibility issues, and often contribute undesirable cosmetics such as prolonged stickiness, difficulty in ease of spreading, increased dry-down times and reduced dry feel after application.

Specific concentrations of the gellant materials can be selected according to the desired penetration force value. For roll-on formulations having a penetration force value of from about 20 gram·force to about 100 gram·force, gellant material concentrations preferably range from about 0.1% to about 3%, preferably from about 1.5% to about 3%, by weight of the antiperspirant composition. For other cream formulations, including those formulations suitable for use in cream applicator devices, which have a penetration force value of from about 100 gram·force to about 500 gram·force, gellant material concentrations preferably range from about 3% to about 8%, preferably from about 3% to about 6%, by weight of the antiperspirant composition.

Specific examples of fatty alcohol gellants for use in the antiperspirant compositions that are commercially available include, but are not limited to, Unilin® 425, Unilin® 350, Unilin® 550 and Unilin® 700 (supplied by Petrolite)

Residue Masking Material

The soft solid compositions can further comprise a non-volatile emollient as a residue masking material. Such materials and their use in antiperspirant products are well known in the antiperspirant art, and any such material may be incorporated into the composition of the present invention, provided that such optional material is compatible with the essential elements of the composition, or does not unduly impair product performance or cosmetics.

Concentrations of the optional residue masking material can range from about 0.1% to about 40%, preferably from about 1% to about 10%, by weight of the antiperspirant composition. These optional materials can be liquid at ambient temperatures, and can be nonvolatile. The term "nonvolatile" as used in this context refers to materials which have a boiling point under atmospheric pressure of at least about 200° C. Nonlimiting examples of suitable residue masking materials for use in the antiperspirant products include butyl stearate, diisopropyl adipate, petrolatum, nonvolatile silicones, octyldodecanol, phenyl trimethicone, isopropyl myristate, C12-15 ethanol benzoates and PPG-14 Butyl Ether. Residue masking materials are described, for example, in U.S. Pat. No. 4,985,238, which description is incorporated herein by reference.

Other Materials

The soft solid compositions can further comprise one, or more, other materials which modify the physical characteristics of the compositions or serve as additional "active" components when deposited on the skin. Many such materials are known in the antiperspirant art and can be used in the antiperspirant compositions herein, provided that such optional materials are compatible with the essential materials described herein, or do not otherwise unduly impair product performance.

Non limiting examples of materials can include active components such as bacteriostats and fungiostats, and "non-active" components such as colorants, perfumes, cosmetic powders, emulsifiers, chelants, distributing agents, preservatives, and wash-off aids. Examples of such optional materials are described in U.S. Pat. No. 4,049,792; Canadian Patent 1,164,347; U.S. Pat. Nos. 5,019,375; and 5,429,816; which descriptions are incorporated herein by reference.

E. Aerosol

An aerosol composition can comprise a concentrate, a propellant, or a combination thereof. Alcohol is a predominant component of the concentrates provided herein. Useful alcohols include $C_1$-$C_3$ alcohols, with the preferred alcohol being ethanol. In certain examples, the alcohol is employed at a concentration level of from at least about 40%, 50% or 55% to about 80%, by weight of the concentrate.

An antiperspirant active is dissolved in the alcohol, at a level of from about 1% to about 15%, by weight of the concentrate. Various antiperspirant actives can be employed, including, for example, aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY. In one example, aluminum chlorohydrex PG is the chosen antiperspirant active.

The antiperspirant concentrates can also include an oil or a mixture of two or more oils. Useful oils include, for example, volatile silicone oils and non-volatile organic oils. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone can be a cyclic silicone having from at least about 3 silicone atoms or from at least about 5 silicone atoms but no more than about 7 silicone atoms or no more than about 6 silicone atoms. For example, volatile silicones can be used which conform to the formula:

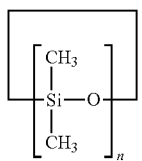

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); MASIL SF-V (available from Mazer) and combinations thereof. Suitable volatile silicone oils can also include linear silicone oils such as, for example, DC200 (1 cSt), DC200 (0.65 cSt), and DC2-1184, all of which are available from Dow Corning Corp. In certain examples, the volatile silicone oil can have a viscosity of less than 10 centistokes at 25° C.

Non-volatile organic, emollient oils can also be employed. A representative, non-limiting list of emollient oils includes CETIOL CC (dicaprylyl carbonate), CETIOL OE (dicaprylyl ether), CETIOL S (diethylhexylcyclohexane), and CETIOL B (dibutyl adipate), all of which are available from Cognis, and LEXFEEL 7 (neopentyl glycol diheptanoate) from Inolex. In certain examples, the organic emollient oils have a viscosity of less than 50 centistokes at 25° C. The term "organic emollient oil" as used herein means silicon-free emollient oils that are liquid at 25° C., and that are safe and light to skin and can be miscible with volatile silicone oils (as described above) and the antiperspirant active-alcohol solution in the concentration ranges described below.

The oil or mixture of oils is generally included in the concentrate formulas at a level of from about 5% to about 45%, by weight of the concentrate. This viscosity ranges noted above in connection with the different classes of oil can facilitate desired spray rates and patterns, and can help minimize nozzle clogging. To provide desired skin feel, minimal nozzle clogging, and good concentrate stability, the ratio of alcohol to volatile silicone oil is preferably greater than 1.0, 1.35, or 1.5. And in examples having both a volatile silicone oil and an organic emollient oil, the ratio of alcohol to total oil is preferably greater than or equal to about 0.90. The oils in certain examples are miscible with the alcohol and antiperspirant active solution. Although various levels of miscibility are acceptable, the oils are preferably miscible enough with the alcohol and antiperspirant active solution to yield a concentrate having a clear appearance.

The antiperspirant compositions can also include residue-masking agents and propellants as discussed above.

Test Methods

The Degree of Habituation to an antiperspirant composition containing a perfume can be determined by exposing a human panel to daily exposures of the perfume over a four week period. The Degree of Habituation can be calculated at both the week two and week four time points, relative to the initial baseline time point.

For each exposure panel test, more than 15 panelists are recruited, and then exposed to the test scent in a manner, frequency, and concentration indicated by the intended product end use, but including at least one exposure per day every day for four consecutive weeks. The perfume exposure must be sufficient that the panelists can detect the perfume of interest being delivered from the product or perfume delivery system contained within the product. The criteria for recruitment onto the exposure panel requires that panelists be typical consumers of the product in question, who agree to use the scent being tested, are non-smokers, and free of nasal congestion and allergies. The degree of habituation is calculated and reported as the percent change in the Odor Detection Threshold (ODT) value at week 2 and at week 4, versus the initial baseline ODT value. Since the degree of habituation is a relative measure, it accommodates the variation in absolute ODT values which can arise between different testing laboratories.

Raw materials and finished products comprising them can be used in conjunction in order to determine the degree of habituation. For example, daily exposures to the panelists may involve the use of a finished product while the ODT test measurements may involve the use of the respective neat perfume or PRMs. The conditions selected for use in either the daily exposures or in the ODT testing must be applied uniformly across all panelists, and remain unchanged for the entirety of the testing period. When the test perfume materials are available in their simple forms i.e., PRMs, neat perfumes, or fine fragrances, unincorporated into complex products or delivery systems, then the ODT test is to be conducted with these simple forms via an olfactometer, as this is the preferred method. When these simple forms of the test perfume materials are inaccessible for testing, then the ODT test may be conducted with finished products or complex formulations comprising the test perfume materials. Presentation devices other than an olfactometer may be required when conducting the ODT testing on finished products or complex formulations, and may include devices such as sniff cups, headspace chambers and capped bottles, as allowed for in the test method ASTM E679-04 described below.

The ODT value for each panelist is determined at each of three time points the during four week daily exposure period, namely; at an initial baseline, at two weeks, and at four weeks. The ODT values are always determined in accordance with test method ASTM E679-04 (Standard Practice for Determination of Odor and Taste Thresholds by a Forced-Choice Ascending Concentration Series of Limits) as reapproved in 2011 except, the following replaces the protocol of such test method's Sub-articles 4.4, 8.2 and 8.3.

Sub-article 4.4, Individual best-estimate values of the threshold are derived from the pattern of correct/incorrect responses produced separately by each panelist. The group average ODT value at a given time point is derived by fitting the entire data set from all panelists at that time point to a Log Logistic Regression Model.

Sub-article 8.2, If the concentration range has been correctly selected, it is not necessary that all panelists judge correctly within the range of concentration steps provided. Thus, the representation of the panelists' judgments as in 8.1 need not terminate with two or more consecutive plusses (+).

Sub-article 8.3, Since there is a finite probability that a correct answer will occur by chance alone, it is important that a panelist repeat the test three times. Panelists who fail the test at the highest concentration, are deemed anomic to the test material and their response is removed from the data set.

Additionally, the following selections are made in accordance with the test method's sub-articles 1.3, 1.4, 1.6, 1.7, and 4.1, and specified here as per sub-article 9.3.

Sub-article 1.3, The threshold is characterized as being a) only detection (awareness) that a very small amount of added substance is present but not necessarily recognizable.

Sub-article 1.4, When the preferred method is being conducted, namely using a simple perfume form presented via olfactometer, then the presentation medium is an air and pure nitrogen mix. When testing finished or complex products, alternative presentation media may be used, such as air.

Sub-article 1.6, When the preferred method is being conducted, namely using a simple perfume form presented via olfactometer, then the physical method of presentation is at a rate of 40 L/min. When testing finished or complex products, alternative presentation devices may be used, including but not limited to sniff cups, headspace chambers or capped bottles.

Sub-article 1.7, Presentation is made to a panel of greater than 15 panelists, who are participating in the daily exposure panel.

Sub-article 4.1, Eight scale steps are used, with each step having an individual predetermined dilution factor suitable for the stimuli being tested, at a temperature of 35° C. PRM or neat perfume stimuli are typically introduced to the olfactometer system in the neat form via a pump syringe. Sometimes a dilution of the stimuli with ethanol is needed.

The group average ODT values from the three time points are used to calculate the degree of habituation. The degree of habituation is reported for 2 specific time points, as the percent change in group average ODT at one time point, relative to the group average ODT at the initial baseline time point. The degree of habituation is determined at the time points of: 2 weeks and 4 weeks, of the four week daily exposure period, using the following formula:

$$\text{Degree of Habituation (percent change in ODT) at Time } X = ((\text{Group Average ODT}_{(Time\ X)} - \text{Group Average ODT}_{(Baseline)})/\text{Group Average ODT}_{(Baseline)}) \times 100$$

where Time X is either 2 weeks, or 4 weeks, of repeated daily exposure.

Anti-Habituation Index

A perfume is considered to have an anti-habituation index of:

For a Two Week Test

Zero (0) when the Degree of Habituation after 2 weeks of exposure to said perfume is from about 150% to 25%

One (1) when the Degree of Habituation after 2 weeks of exposure to said perfume is less than 25% but greater than 10%;

Two (2) when the Degree of Habituation after 2 weeks of exposure to said perfume is from 10% to 0%; or Three (3) when the Degree of Habituation after 2 weeks of exposure to said perfume is less than 0% to about −25%.

Four (4) when the Degree of Habituation after 2 weeks of exposure to said perfume is less than −25% to about −500%

For a Four Week Test

Zero (O) when the Degree of Habituation after 4 weeks of exposure to said perfume is from about 150% to 25%

One (1) when the Degree of Habituation after 4 weeks of exposure to said perfume is less than 25% but greater than 10%;

Two (2) when the Degree of Habituation after 4 weeks of exposure to said perfume is from 10% to 0%; or Three (3) when the Degree of Habituation after 4 weeks of exposure to said perfume is less than 0% to about −25%.

Four (4) when the Degree of Habituation after 4 weeks of exposure to said perfume is less than −25% to about −500%

EXAMPLES

While particular examples of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention. Weight percentages are intended in the examples below, unless otherwise denoted.

Example 1

Example Anhydrous Stick Compositions that Resist Habituation, Excluding Formula IV

|  | Formula I Invisible Solid | Formula II Invisible Solid | Formula III Invisible Solid | Formula IV Soft Solid | Formula V Soft Solid | Formula VI Soft Solid |
| --- | --- | --- | --- | --- | --- | --- |
| Aluminum Zirconium Trichlorohydrex Glycine Powder | 24 | 24 | 24 | 26.5 | 26.5 | 26.5 |
| Cyclopentasiloxane | Q.S | Q.S. | Q.S. | Q.S. | Q.S. | Q.S. |
| Dimethicone | — | — | — | 5 | 5 | 5 |
| CO-1897 Stearyl Alcohol NF | 14 | 14 | 14 | — | — | — |
| Hydrogenated Castor Oil MP80 Deodorized | 3.85 | 3.85 | 3.85 | — | — | — |
| Behenyl Alcohol | 0.2 | 0.2 | 0.2 | — | — | — |
| Tribehenin | — | — | — | 4.5 | 4.5 | 4.5 |
| C 18-36 acid triglyceride | — | — | — | 1.125 | 1.125 | 1.125 |
| C12-15 Alkyl Benzoate | 9.5 | 9.5 | 5 | — | — | — |
| PPG-14 Butyl Ether | 6.5 | 6.5 | — | 0.5 | 0.5 | 0.5 |
| Phenyl Trimethicone | 3 | — | 3 | — | — | — |
| White Petrolatum | 3 | — | — | 3 | 3 | 3 |
| Mineral Oil | 1.0 | 1.0 | 1.0 | — | — | — |
| Typical Perfume | 0.5 | — | — | 0.9 | — | — |
| Marketed Perfume | — | — | — | — | — | 0.75 |
| Perfume Table 1 | 0.5 | 1.1 | 0.9 | — | 1.0 | — |
| Beta-Cyclodextrin complexed with perfume Table 1 | — | 3.0 | — | — | — | 3.0 |
| Talc Imperial 250 USP | 3.0 | 3.0 | 3.0 | — | — | — |
| Polyacrylate Microcapsule loaded with perfume Table 1 | — | — | 1.9 | — | — | — |

Q.S. - indicates that this material is used to bring the total to 100%.

With the exception of Formula IV, the formulations set forth above contain perfume from Table 1 at various levels, optionally using various perfume delivery systems. Formula III contains perfume from Table 1 contained in a polyacrylate microcapsule, as described above in Polymer-Assisted Delivery, Reservoir Systems. Formula VI contained perfume from Table 1, as described above in the cyclodextrin delivery systems.

Test subjects were recruited for the following study, based on their acceptance of the scent of the products in Formulas IV, V, and VI above. Approximately 20 test subjects per usage group were recruited for the study. The test subjects placed in the study were assessed for their baseline threshold intensity according to the Odor Detection Threshold (ODT) method defined above for the perfume of interest that was in the product. Test subjects were placed in three study groups with an antiperspirant/deodorant according to Formulas IV, V, and VI and instructed to apply 2 clicks per underarm (approximately 0.4 g per underarm) throughout the four week study period, using no other underarm products throughout the duration of the study. Their Odor Detection Threshold (ODT) was measured again after 2 weeks of usage, and again after 4 weeks of usage. The average Odor Detection Threshold was calculated for each usage group. Results are shown below.

The results indicate that the Odor Detection Threshold increases significantly above baseline (test subjects are less sensitive) for the usage group using Formula IV (comparative perfume) after 4 weeks of usage, indicating habituation.

A surprising result is that the Odor Detection Threshold remains below baseline for each usage group using Formula V and Formula VI that contain the perfume from Table 1, indicating that they did not become habituated to the scent of the product over time. Therefore, the perfume used in Formulas V and VI have an anti-habituation index of 4 and 3, respectively, when tested in a two week test, and an anti-habituation index of 4 and 4, respectively, when tested in a four week test.

Degree of Habituation (% change in group average ODT)

| Product Used | Type of Perfume Run in the ODT test | % Change in ODT at Week 2 | % Change in ODT at Week 4 |
| --- | --- | --- | --- |
| Formula IV from Example 1 | Comparative Perfume | 41% | 634% |
| Formula V from Example 1 | Perfume from Table 1 | −86% | −29% |
| Formula VI from Example 1 | Perfume from Table 1 | −24% | −91% |

Example 2

Anhydrous Stick Compositions that Resist Habituation

TABLE 2

| Base Perfume Formulation PD | | |
|---|---|---|
| Ingredient | Percent | CAS# |
| 2 6 Nonadienol 10% In DPG | 0.20% | |
| Allyl Amyl Glycolate | 0.10% | 67634-00-8 |
| Allyl Cyclohexane Propionate | 0.50% | 2705-87-5 |
| Allyl Heptoate | 1.00% | 142-19-8 |
| Ambrettolide | 0.50% | 28645-51-4 |
| Anisic Aldehyde | 0.10% | 123-11-5 |
| Benzaldehyde | 0.05% | 100-52-7 |
| Benzoin Siam Resinoid 50% Mpg Ref A | 0.20% | 9000-72-0 |
| Benzyl Acetate | 3.00% | 140-11-4 |
| Benzyl Salicylate | 5.00% | 118-58-1 |
| Beta Gamma Hexenol | 0.20% | 928-96-1 |
| Cashmeran | 0.20% | 33704-61-9 |
| Cinnamic Alcohol | 0.10% | 104-54-1 |
| Cis 3 Hexenyl Acetate | 0.30% | 3681-71-8 |
| Cis-3-Hexenyl Salicylate | 1.00% | 65405-77-8 |
| Cis-6-Nonen-1-OL FCC | 0.05% | 35854-86-5 |
| Citronellol | 0.30% | 106-22-9 |
| Citronellyl Acetate | 0.10% | 150-84-5 |
| Citronellyl Oxyacetaldehyde | 0.04% | 7492-67-3 |
| Cyclo Galbanate | 0.10% | 68901-15-5 |
| Cymal | 4.00% | 103-95-7 |
| Delta Damascene | 0.20% | 57378-68-4 |
| Delta Muscenone 962191 | 0.10% | 63314-79-4 |
| Dihydro Myrcenol | 2.00% | 18479-58-8 |
| Dimethyl Benzyl Carbinyl Acetate | 0.50% | 151-05-3 |
| Ethyl 2 Methyl Pentanoate | 0.30% | 39255-32-8 |
| Ethyl Acetoacetate | 0.50% | 141-97-9 |
| Ethyl Maltol | 0.40% | 4940-11-8 |
| Ethyl-2-Methyl Butyrate | 0.10% | 7452-79-1 |
| Ethylene Brassylate | 7.00% | 105-95-3 |
| Floralozone | 0.50% | 67634-15-5 |
| Gamma Decalactone | 0.50% | 706-14-9 |
| Geranyl Acetate | 0.20% | 105-87-3 |
| Helional | 1.00% | 1205-17-0 |
| Heliotropin | 0.10% | 120-57-0 |
| Hexamethylindanopyran | 10.00% | 1222-05-5 |
| Hexyl Acetate | 0.50% | 142-92-7 |
| Hexyl Cinnamic Aldehyde | 7.00% | 101-86-0 |
| Hydroxycitronellal | 3.00% | 107-75-5 |
| Indolene | 0.20% | 68908-82-7 |
| Ionone Gamma Methyl | 5.00% | 127-51-5 |
| Iso E Super Or Wood | 10.00% | 54464-57-2 |
| Iso Eugenol | 0.05% | 97-54-1 |
| Jasmolactone | 0.10% | 32764-98-0 |
| Laevo Trisandol | 2.00% | 28219-61-6 |
| Liffarome | 0.40% | 67633-96-9 |
| Ligustral Or Triplal | 0.20% | 68039-49-6 |
| Linalool | 5.00% | 78-70-6 |
| Linalyl Acetate | 3.00% | 115-95-7 |
| Lyral | 2.00% | 31906-04-4 |
| Melonal | 0.20% | 106-72-9 |
| Methyl Dihydro Jasmonate | 10.00% | 24851-98-7 |
| Methyl Pamplemousse | 0.30% | 67674-46-8 |
| Methyl Phenyl Carbinyl Acetate | 0.40% | 93-92-5 |
| Methyl-2-Nonenoate | 0.10% | 111-79-5 |
| Nerolidol | 0.50% | 7212-44-4 |
| Oil Lemon Brazilcp Select Fcc Enh 15130 | 1.00% | 8008-56-8 |
| Orivone | 0.20% | 16587-71-6 |
| Para Hydroxy Phenyl Butanone | 1.00% | 5471-51-2 |
| Phenyl Ethyl Alcohol | 0.50% | 60-12-8 |
| Phenyl Ethyl Phenyl Acetate | 0.05% | 102-20-5 |
| Pino Acetaldehyde | 0.05% | 33885-51-7 |
| Polysantol | 0.20% | 107898-54-4 |
| Precyclemone B | 0.30% | 52475-86-2 |
| Prenyl Acetate | 0.20% | 1191-16-8 |
| *Prunella* | 0.10% | |
| Synambran R 50% In IPM* | 0.20% | |
| Undecalactone | 2.00% | 104-67-6 |
| Undecavertol | 0.50% | 81782-77-6 |
| Undecylenic Aldehyde | 0.01% | 112-44-7 |
| Vanillin | 0.30% | 121-33-5 |
| Verdox | 3.00% | 88-41-5 |

*Supplied by Symrise GmbH, with offices located at Muhlenfeldstrasse 1, Holzminden, 37603, Germany

TABLE 3

| Control Perfume Formulation PD with additional perfume raw materials | | | |
|---|---|---|---|
| | Perfume 2.A | Perfume 2.B | Perfume 2.C |
| Base Control Perfume Formulation PD from Table 2 | 99.9987% | 99.94% | 93.5% |
| 5-Mercapto-5-Methyl-3-hexanone | 0.001% | | |
| P-Mentha-8-Thiol-3-One | 0.00025% | | |
| 1-para-menthene-8-thiol | 0.00005% | | |
| 2-(4-methyl-1,3-thiazol-5-yl)ethanol | | 0.05% | |
| 2-(2-methylpropyl)-1,3-thiazol | | 0.005% | |
| 4-methyl-2-propan-2-yl-1,3-thiazole | | 0.005% | |
| (1R,2S,5R)-5-methyl-2-propan-2-ylcyclohexan-1-ol | | | 5.0% |
| [(1R,2S,5R)-5-methyl-2-propan-2-ylcyclohexyl] acetate | | | 1.0% |
| (2R,5R)-5-methyl-2-(propan-2-yl)cyclohexanone | | | 0.5% |

TABLE 4

| Soft Solid Antiperspirant Compositions | | | | |
|---|---|---|---|---|
| | Formula VII Soft Solid | Formula VIII Soft Solid | Formula IX Soft Solid | Formula X Soft Solid |
| Aluminum Zirconium Trichlorohydrex Glycine Powder | 26.5 | 26.5 | 26.5 | 26.5 |
| Cyclopentasiloxane | Q.S. | Q.S. | Q.S. | Q.S. |
| Dimethicone | 5 | 5 | 5 | 5 |
| Tribehenin | 4.5 | 4.5 | 4.5 | 4.5 |
| C 18-36 acid triglyceride | 1.125 | 1.125 | 1.125 | 1.125 |
| PPG-14 Butyl Ether | 0.5 | 0.5 | 0.5 | 0.5 |
| White Petrolatum | 3 | 3 | 3 | 3 |
| Base Control Perfume Formulation | 0.8 | — | — | — |
| Perfume 2.A | — | 0.8 | — | — |
| Perfume 2.B | — | — | 0.8 | — |
| Perfume 2.C | — | — | — | 0.8 |

Q.S. - indicates that this material is used to bring the total to 100%.

The formulations defined above various perfume formulations. Formula VII contains a base control perfume formulation PD. Formulas VIII, IX, and X each contain additional components. More specifically, formula VIII containing Perfume 2.A includes a three component perfume accord composed of perfume raw materials containing a thiol moiety. Formula IX containing Perfume 2.B includes a three component perfume accord composed of perfume raw materials containing a thiazole moiety. Formula X containing Perfume 2.C includes a three component perfume accord composed of perfume raw materials consisting of menthol and menthol derivatives.

Approximately 20 test subjects per usage group were recruited for the study. The test subjects placed in the study were assessed for their baseline threshold intensity according to the Odor Detection Threshold (ODT) method defined above for the perfume of interest that was in the product. Test subjects were placed in five study groups with an antiperspirant/deodorant according to Formulas VII, VIII, IX, and X, and instructed to apply 2 clicks per underarm (approximately 0.4 g per underarm) throughout the four week study period, using no other underarm products throughout the duration of the study. Their Odor Detection Threshold (ODT) was measured again after 2 weeks of usage, and again after 4 weeks of usage. The average Odor Detection Threshold was calculated for each usage group. Results are shown below.

The results indicate that the Odor Detection Threshold remains unchanged for the usage group using Formula VII (comparative perfume) after 4 weeks of usage. The Odor Detection Threshold increases significantly above baseline (test subjects are less sensitive) for the usage group using Formula X (perfume containing menthol and menthol derivatives) after 4 weeks of usage, indicating habituation. One surprising result is that the base perfume's (Formula VII) anti-habituation index of two (2) from the two week test moved, when anti-habituation materials were added (formulations VIII, and IX) to an anti-habituation indices for such formulas of, 4, and 3 respectively under the two week test when the additional perfume raw materials(s) as specified in Perfume 2.A, and Perfume 2.B are added. Another surprising result is that the base perfume's (Formula VII) anti-habituation index of three (3) from the four week test moved, when anti-habituation materials were added (formulations VIII, and IX) to an anti-habituation indices for such formulas of, 4, and 4 respectively under the four week test when the additional perfume raw materials(s) as specified in Perfume 2.A, and Perfume 2.B are added. Such materials were a thiol accord, and thiazole accord.

TABLE 5

Degree of Habituation (% change in group average ODT)

| Product Used | Type of Perfume Run in the ODT Test | % Change in ODT at Week 2 | % Change in ODT at Week 4 |
|---|---|---|---|
| Formula VII | Base Perfume Formulation PD | 2% | -2% |
| Formula VIII | Perfume 2.A - Base Control Perfume Formulation PD comprising Thiol Accord | -86% | -93% |
| Formula IX | Perfume 2.B Base Control Perfume Formulation PD comprising Thiazole Accord | -6% | -62% |
| Formula X | Perfume 2.C Base Control Perfume Formulation PD comprising menthol and menthol derivative Accord | 96% | 1052% |

The above Formulas VII, VIII, IX, and X were rated by consumers in a usage test. Ten independent test groups of approximately 20 panelists were instructed to use the product as they normally would. Five of the test groups, each using one of the Formulas VII, VIII, IX, and X were instructed to use the product for a single day, and rate their overall opinion of the product after using the product based on a 5 point scale. (100=Excellent, 75=Very Good, 50=Good, 25=Fair, 0=Poor). Separately, the other five test groups, each using one of the Formulas VII, VIII, IX, and X, were instructed to use the product for a four week period, and rate their overall opinion of the product based on the same 5 point scale defined above. Results indicate that formulas are rated parity after a single day usage, but the resistance to habituation shown in Table 5 yields an improved usage rating, only after a four week period.

TABLE 6

|  | Formula VII | Formula VIII | Formula IX | Formula X |
|---|---|---|---|---|
| Overall Rating Single Day Use | 64 | 57 | 65 | 66 |
| Overall Rating 4 Week Use | 66 | 69 | 80 | 70 |
| Delta of single day vs. 4 week ratings | +2 | +12 | +15 | +4 |

Example 3: Anhydrous Stick Compositions that Resist Habituation

TABLE 7

Soft Solid Antiperspirant Compositions

|  | Formula XI Soft Solid | Formula XII Soft Solid | Formula XIII Soft Solid |
|---|---|---|---|
| Aluminum Zirconium Trichlorohydrex Glycine Powder | 26.5 | 26.5 | 26.5 |
| Cyclopentasiloxane | Q.S. | Q.S. | Q.S. |
| Dimethicone | 5 | 5 | 5 |
| Tribehenin | 4.5 | 4.5 | 4.5 |
| C 18-36 acid triglyceride | 1.125 | 1.125 | 1.125 |
| PPG-14 Butyl Ether | 0.5 | 0.5 | 0.5 |
| White Petrolatum | 3 | 3 | 3 |
| Beta-Cyclodextrin complexed with perfume | — | — | 3 |
| Perfume (defined in Table 8) | 0.9 | — | — |
| Comparative Perfume A | — | 0.9 | — |
| Comparative Perfume C | — | — | 1.5 |

Q.S. - indicates that this material is used to bring the total to 100%.

TABLE 8

| Example Number | Base Perfume Formulation PD Level from Table 2 | Anti-habituating Material | CAS Number of Anti-habituating Material | Percent of Anti-habituating Material in perfume |
|---|---|---|---|---|
| XI.A | 100% | — | — | — |
| XI.B | 99.998 | Sauvignone 100* | 851768-51-9 | 0.00002 |
| XI.C | 99.98 | Sauvignone 100* | 851768-51-9 | 0.0002 |
| XI.D | 99.8 | Sauvignone 100* | 851768-51-9 | 0.002 |
| XI.E | 99.5 | 4,7,7-trimethyl-6-thiabicyclo[3.2.1]octane | 68398-18-5 | 0.5 |
| XI.F | 99.998 | 1-butylsulfanylbutane | 544-40-1 | 0.002 |
| XI.G | 99.98 | 1-butylsulfanylbutane | 544-40-1 | 0.02 |
| XI.H | 99.9 | 1-(1,3-thiazol-2-yl)ethanone | 24295-03-2 | 0.1 |
| XI.I | 99.98 | (2R,4S)-2-methyl-4-propyl-1,3-oxathiane | 59323-76-1 | 0.02 |
| XI.J | 99.9 | (2R,4S)-2-methyl-4-propyl-1,3-oxathiane | 59323-76-1 | 0.2 |
| XI.K | 99.9975 | 2-methyl-3-methylsulfanylpyrazine | 67952-65-2 | 0.0025 |

*Sauvignone 100 is supplied as a 1% active containing 5-methyl-5-sulfanylhexan-3-one The formulations defined in Table 8 are various perfume formulations to be used in Formula XI. Eleven unique formulas were made from Formula XI, each containing 0.9% of one of the perfumes from example number XI.A through XII.K, as defined in Table 8.

Approximately 20 test subjects per usage group were recruited for the study. The test subjects placed in the study were assessed for their baseline threshold intensity according to the Odor Detection Threshold (ODT) method defined above for the perfume of interest that was in the product. Test subjects were placed in nineteen study groups with an antiperspirant/deodorant and instructed to apply 2 clicks per underarm (approximately 0.4 g per underarm) throughout the four week study period, using no other underarm products throughout the duration of the study. Their Odor Detection Threshold (ODT) was measured again after 4 weeks of usage. The average Odor Detection Threshold was calculated for each usage group. Results are shown below.

The results indicate that the Odor Detection Threshold increases significantly above baseline (test subjects are less sensitive) for the usage group using the formula containing the base perfume PD only, which was void of all sulfur and nitrogen PRM's after 4 weeks of usage, indicating habituation. Surprisingly, all components containing sulfur or nitrogen chemistry showed improvement relative to the control. The data further suggests that molecules containing sulfur or nitrogen having a sulfide moiety, thiazole moiety, oxime moiety, or acetyl group produce the highest resistance to habituation, therefore have the highest anti-habituation index at levels below and above threshold

TABLE 9

| | Degree of Habituation (% change in group average ODT) Results: | | | |
|---|---|---|---|---|
| Product Used | Pink Daisy Perfume + Antihabituating material defined below for ODT Test | Chemical Moiety of Antihabituating Material | % Change in ODT at Week 4 | Anti-habituation Index for four week test |
| Formula XII Containing XII.A | — | | 3554 | Highly Habituating, thus no index |
| Formula XI containing XI.B | Sauvignone 100 (below threshold) | Thiol | 166 | Habituating, thus no index |
| Formula XI containing XI.C | Sauvignone 100 (above threshold) | Thiol | 728 | Habituating, thus no index |
| Formula XI containing XI.D | Sauvignone 100 (saturation point) | Thiol | 364 | Habituating, thus no index |
| Formula XI containing XI.E | 4,7,7-trimethyl-6-thiabicyclo[3.2.1]octane (above threshold) | Sulfide | −61 | 4 |
| Formula XI containing XI.F | 1-butylsulfanylbutane (below threshold) | Sulfide | −63 | 4 |
| Formula XI containing XI.G | 1-butylsulfanylbutane (above threshold) | Sulfide | −31 | 4 |
| Formula XI containing XI.H | 1-(1,3-thiazol-2-yl)ethanone (above threshold) | Thiazole | −59 | 4 |
| Formula XI containing XI.I | (2R,4S)-2-methyl-4-propyl-1,3-oxathiane (below threshold) | Oxathiane | 413 | Habituating, thus no index |
| Formula XI containing XI.J | (2R,4S)-2-methyl-4-propyl-1,3-oxathiane (above threshold) | Oxathiane | 218 | Habituating, thus no index |
| Formula XI containing | 2-methyl-3-methylsulfanylpyrazine | Pyrazine comprising a | −88 | 4 |

TABLE 9-continued

Degree of Habituation (% change in group average ODT) Results:

| Product Used | Pink Daisy Perfume + Antihabituating material defined below for ODT Test | Chemical Moiety of Antihabituating Material | % Change in ODT at Week 4 | Anti-habituation Index for four week test |
|---|---|---|---|---|
| XII.K | (above threshold) | Sulfide moiety | | |
| Formula XII | Contains Comparative Perfume A Only | | 111 | Habituating, thus no index |
| Formula XIII | Contains Comparative Perfume C Only | | 405 | Habituating, thus no index |

It is believed that the differences seen from Example 2, in which the base perfume had an anti-habituation index of 3 in the four week test, vs. Example 3, in which the base perfume had significant increase in ODT is beyond what is expected of individual variation among panelists and were related to the difference in perfume level (0.8% vs. 0.9%). Further, it is believed that the base perfume would be habituating, even at a lower perfume level if the test subjects used the product for a longer duration. The addition of sulfur and nitrogen PRM's consistently showed greater resistance to habituation as compared to the control—regardless of perfume level tested.

Example 4: Deodorant Compositions

TABLE 10

| Ingredient | Formula XIV | Formula XV | Formula XVI | Formula XVII | Formula XVIII |
|---|---|---|---|---|---|
| | Product Form | | | | |
| | Solid Deodorant | Solid Deodorant | Solid Deodorant | Solid Deodorant | Aerosol Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG -8 | | | | 20 | |
| ethanol | | | | | Q.S. |
| Water | Q.S. | Q.S. | Q.S. | Q.S. | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Perfume Table 1 | 0.5 | 1.0 | 1.0 | 0.5 | 1.5 |
| Propellant (1,1 difluoroethane) | | | | | 40 |

Q.S.—indicates that this material is used to bring the total to 100%.

Example 4 discloses five formulations for antiperspirant compositions that resist habituation. Table 10 discloses four formulations that are solid deodorant sticks and one aerosol body spray in Formula XVIII.

All documents cited in the Detailed Description are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern. The perfume raw materials disclosed, claimed and/or used in the perfumes claimed and/or described herein encompass any stereoisomers of such perfume raw materials.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antiperspirant composition comprising a perfume, the perfume comprising, based on total perfume weight, from about 0.000001% to about 0.035% of a perfume raw material, the perfume raw material comprises a sulfur atom, such that the perfume raw material resists the fragrance habituation of a consumer to the antiperspirant composition.

2. The antiperspirant composition of claim 1, wherein the perfume raw material further comprises one or more of an oxygen atom and a nitrogen atom.

3. The antiperspirant composition of claim 1 has a four-week anti-habituation index of 3 or greater.

4. An antiperspirant composition comprising a perfume, the perfume comprising, based on total perfume weight, a perfume raw material selected from the group consisting of:
   a. from about 0.0000001% to about 10%, of a perfume raw material comprising a thiol moiety;
   b. from about 0.0000001% to about 0.035%, of a perfume raw material comprising a sulfide moiety;
   c. from about 0.0000001% to about 10%, of a perfume raw material comprising a thiazole moiety;
   d. from about 0.0000001% to about 10%, of a perfume raw material comprising an oxathiane moiety;
   e. from about 0.0000005% to about 5%, of a perfume raw material comprising an isothiocyanate;
   f. from about 0.000001% to about 10%, of a perfume raw material comprising a oxygen, sulfur, and nitrogen; and
   g. mixtures thereof;
such that the perfume raw material resists the fragrance habituation of a consumer to the antiperspirant composition.

5. The antiperspirant composition of claim 4, wherein the perfume raw material is selected from the group consisting of:
   a. from about 0.00001% to about 1%, of the perfume raw material comprising the thiol moiety;
   b. from about 0.00001% to about 0.035%, of the perfume raw material comprising the sulfide moiety;
   c. from about 0.0005% to about 1%, of the perfume raw material comprising the thiazole moiety;
   d. from about 0.00001% to about 1%, of the perfume raw material comprising the oxathiane moiety;
   e. from about 0.000001% to about 1%, of the perfume raw material comprising the isothiocyanate; and
   f. from about 0.0005% to about 1%, of the perfume raw material comprising the oxygen, sulfur, and nitrogen.

6. The antiperspirant composition of claim 4, wherein:
the thiol moiety is selected from the group consisting of 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; methanethiol; ethanethiol; prop-2-ene-1-thiol; propane-2-thiol; 2-methylpropane-2-thiol; propane-1-thiol; butane-2-thiol; butane-1-thiol; 2-methylpropane-1-thiol; methyldisulfanylmethane; 2-methylbutane-2-thiol; 3-methylbutane-2-thiol; 3-methylbutane-2-thiol; pentane-2-thiol; pentane-1-thiol; 2-methylbutane-1-thiol; cyclopentanethiol; 3-methyldisulfanylprop-1-ene; methylsulfanyldisulfanylmethane; 1-methyldisulfanylpropane; ethane-1,2-dithiol; 1-(methyldisulfanyl)prop-1-ene; 3-sulfanylbutan-2-one; ethyldisulfanylethane; hexane-1-thiol; 1-ethyldisulfanylpropane; thiophene-2-thiol; propane-1,3-dithiol; 3-sulfanylpentan-2-one; 2-propan-2-yldisulfanylpropane; butane-1,4-dithiol; benzenethiol; ethylsulfanyldisulfanylethane; 3-methylsulfanyldisulfanylprop-1-ene; 1-methylsulfanyldisulfanylpropane; butane-2,3-dithiol; 4-methyl-4-sulfanylpentan-2-one; 3-prop-2-enyldisulfanylprop-1-ene; 1-methoxyhexane-3-thiol; ethyl 2-sulfanylpropanoate; 1-(prop-2-enyldisulfanyl)propane; 1-propyldisulfanylpropane; 1-(4-hydroxy-3-methoxyphenyl)ethanone butane-1,3-dithiol; 1-propyldisulfanylprop-1-ene; 2-methylbenzenethiol; thiophen-2-ylmethanethiol; 3-sulfanylbutan-2-ol; phenylmethanethiol pentane-1,5-dithiol; 2-ethylbenzenethiol; 3-prop-2-enylsulfanyldisulfanylprop-1-ene; methyldisulfanyldisulfanylmethane; 1-propylsulfanyldisulfanylpropane; 2,7,7-trimethylbicyclo [3.1.1] heptane-2-thiol; 2,6-dimethylbenzenethiol; 2-phenylethanethiol; hexane-1,6-dithiol; 2-(methyldisulfanylmethyl)furan; pyridin-2-ylmethanethiol; 2-methoxybenzenethiol; (7,7-dimethyl-2-bicyclo [3.1.1]heptanyl)methanethiol; methyldisulfanylbenzene; 1-butyldisulfanylbutane; (4-methoxyphenyl)methanethiol; 2-sulfanylpropanoic acid; ethyl 2-methyldisulfanylpropanoate; (2E)-3,7-dimethylocta-2,6-diene-1-thiol; 3,7-dimethylocta-2,6-diene-1-thiol; pyrazin-2-ylmethanethiol; methyldisulfanylmethylbenzene; 2-methyl-5-(1-sulfanylpropan-2-yl)cyclohexane-1-thiol; octane-1,8-dithiol; 2-pyrazin-2-ylethanethiol; naphthalene-2-thiol; 2-oxo-3-sulfanylpropanoic acid; 2-thiophen-2-yldisulfanylthiophene; cyclohexyldisulfanylcyclohexane; 2-(furan-2-ylmethyldisulfanylmethyl)furan; phenyldisulfanylbenzene; benzyldisulfanylmethylbenzene; 8-Hydroxy-5-quinolinesulfonic acid; bis(3-methylbutyl) 2-sulfanylbutanedioate; 2-aminoethanesulfonic acid; 2-phenyl-3H-benzimidazole-5-sulfonic acid; 2-methyl-2-sulfanylpentan-1-ol; and mixtures thereof;
the sulfide moiety is selected from the group consisting of 1-butylsulfanylbutane; ethyl 3-methylsulfanylpropanoate; 2-(methylsulfanylmethyl)furan; methylsulfanylmethane; methylsulfanylethane; 3-methylsulfanylprop-1-ene; S-methyl ethanethioate; ethylsulfanylethane; 1-methylsulfanylpropane; S-ethyl ethanethioate; 1-methylsulfanylbutane; 2-propan-2-ylsulfanylpropane; bis(methylsulfanyl)methane; 1-ethylsulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methylsulfanylacetate; S-prop-2-enyl propanethioate; 1-methylsulfanylbutan-2-one; 4-methylsulfanylbutan-2-one; 3-methylsulfanylpropan-1-am; 2,4,6-trimethyl-1,3,5-trithiane; 3-methylsulfanylbutanal; 2-methyl-1,3-thiazolidine; 2-methyl-4,5-dihydro-1,3-thiazole; ethyl 2-methylsulfanylacetate; methyl 3-methylsulfanylpropanoate; S-propan-2-yl 3-methylbutanethioate; 4-methyl-4-methylsulfanylpentan-2-one; 2-methyl-1,3-dithiolane; methyl 2-methylsulfanylbutanoate; S-methyl furan-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl) methanethioate; 1,2,4-trithiolane; 2-methylthiolan-3-one; 4-methylsulfanylbutan-1-ol; S-butan-2-yl 3-methylbutanethioate; S-butan-2-yl 3-methylbut-2-enethioate; S-(furan-2-ylmethyl) ethanethioate; 2-propyl-1,3-thiazolidine; 3-methyl-1,1-bis(methylsulfanyl)butane; 3-ethylsulfanylpropan-1-ol; S-methyl benzenecarbothioate; 3,5-dimethyl-1,2,4-trithiolane; S-butan-2-yl 2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl) propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl)ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methylsulfanylhexan-1-ol; 2-methyl-4,5-dihydrofuran-3-thiol acetate; 4-(3-oxobutylsulfanyl)butan-2-one; 3-methylsulfanylbutanoic acid; 2-methylsulfanylpyrazine; 2-methyl-3-methylsulfanylpyrazine; 2-(furan-2-ylmethylsulfanylmethyl)furan; 2-(methylsulfanylmethyl)pyrazine; 3,5-di(propan-2-yl)-1,2,4-trithiolane; 2-methylsulfanylphenol; 2-methyl-3-methylsulfanylpyrazine; ethyl 3-(furan-2-ylmethylsulfanyl)propanoate; 2,2,4,4,6,6-hexamethyl-1,3,5-trithiane; 2-methyl-5,7-dihydrothieno[3,4-d]pyrimidine; 2-amino-4-methylsulfanylbutanoic acid; (2S)-2-amino-4-methylsulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; Methyl 2-thiofuroate; and mixtures thereof;

the thiazole moiety is selected from the group consisting of 2-(2-methylpropyl)-1,3-thiazole; 2-(4-methyl-1,3-thiazol-5-yl)ethanol; 4-methyl-2-propan-2-yl-1,3-thiazole; 1-(1,3-thiazol-2-yl)ethanone; 2,4,5-Trimethylthiazole; 2-isopropyl-4-methylthiazole; 4-vinyl-5-methylthiazole; 2,4-Dimethyl-5-acetylthiazole 1,3-thiazole; 4-methyl-1,3-thiazole; 2,4-dimethyl-1,3-thiazole; 4,5-dimethyl-1,3-thiazole; 2,5-dimethyl-1,3-thiazole; 5-ethenyl-4-methyl-1,3-thiazole; 2-ethyl-4-methyl-1,3-thiazole; 4-ethyl-2-methyl-1,3-thiazole; 2-propyl-1,3-thiazole; 2,4,5-trimethyl-1,3-thiazole; 2-ethyl-1,3-thiazole; 2-ethoxy-1,3-thiazole; 2-butan-2-yl-1,3-thiazole; 5-methoxy-2-methyl-1,3-thiazole; 2-ethyl-4,5-dimethyl-1,3-thiazole; 1,3-benzothiazole; 2,5-diethyl-4-methyl-1,3-thiazole; 1-(1,3-thiazol-2-yl)propan-1-one; 4,5-dimethyl-2-(2-methylpropyl)-1,3-thiazole; 2-methyl-1,3-benzothiazole; 1-(2,4-dimethyl-1,3-thiazol-5-yl)ethanone; 4-methyl-2-propan-2-yl-1,3-thiazole; and mixtures thereof;

the oxathiane moiety is selected from the group consisting of (2R,4S)-2-methyl-4-propyl-1,3-oxathiane, 2-methyl-4-propyl-1,3-oxathiane, 2-pentyl-4-propyl-1,3-oxathiane; and mixtures thereof; and the perfume raw material comprising oxygen, sulfur, and nitrogen is selected from the group consisting of 2-(4-methyl-1,3-thiazol-5-yl)ethanol; 1-(1,3-thiazol-2-yl)ethanone; 6-methyl-7-Oxa-1-thia-4-azaspiro[4.4]nonane; 2-[(furan-2-ylmethyl)sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3-thiazol-2-yl)ethanone; 1-(1,3-thiazol-2-yl)propan-1-one; 1-(2,4-dimethyl-1,3-thiazol-5-yl)ethanone; 2-amino-4-methylsulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid; and mixtures thereof.

7. The antiperspirant composition of claim 6, wherein:
the thiol moiety is selected from the group consisting of 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; and mixtures thereof;
the sulfide moiety is selected from the group consisting of 1-butylsulfanylbutane; ethyl 3-methylsulfanylpropanoate; 2-(methylsulfanylmethyl)furan; and mixtures thereof;
the thiazole moiety is selected from the group consisting of 2-(2-methylpropyl)-1,3-thiazole; 2-(4-methyl-1,3-thiazol-5-yl)ethanol; 4-methyl-2-propan-2-yl-1,3-thiazole; 4-methyl-2-propan-2-yl-1,3-thiazole; 1-(1,3-thiazol-2-yl)ethanone; and mixtures thereof;
the oxathiane moiety is (2R,4S)-2-methyl-4-propyl-1,3-oxathiane; and the perfume raw material comprising oxygen, sulfur, and nitrogen is selected from the group consisting of 2-(4-methyl-1,3-thiazol-5-yl)ethanol, 1-(1,3-thiazol-2-yl)ethanone; 6-methyl-7-Oxa-1-thia-4-azaspiro[4.4]nonane; and mixtures thereof.

8. The antiperspirant composition of claim 4, wherein the perfume raw materials are:
(a) 5-mercapto-5-methyl-3-hexanone; p-mentha-8-thiol-3-one; and 1-para-menthene-8-thiol; or
(b) 2-(4-methyl-1,3-thiazol-5-yl)ethanol; 2-(2-methylpropyl)-1,3-thiazol; and 4-methyl-2-propan-2-yl-1,-3-thiazole.

9. The antiperspirant composition of claim 4 has a four-week anti-habituation index of 3 or greater.

10. The antiperspirant composition of claim 4 exhibits an anti-habituating effect on a consumer.

11. The antiperspirant composition of claim 4 is a stick antiperspirant.

12. The antiperspirant of claim 11, wherein the stick antiperspirant is an anhydrous stick, an invisible stick, or a soft solid.

13. The antiperspirant composition of claim 4, wherein the composition is a body spray, clear gel, or aerosol antiperspirant.

14. The antiperspirant composition of claim 4 is a roll on antiperspirant.

15. The antiperspirant composition of claim 4, wherein the antiperspirant composition further comprises a perfume delivery system configured to deliver the perfume and perfume raw materials.

16. The antiperspirant composition of claim 4, further comprising a perfume raw material comprising a nitrogen atom.

17. The antiperspirant composition of claim 16, wherein the perfume raw material comprising a nitrogen atom is (NE)-N-[(6E)-2,4,4,7-tetramethylnona-6,8-dien-3-ylidene]hydroxylamine).

* * * * *